(12) United States Patent
Mitani et al.

(10) Patent No.: US 7,803,579 B2
(45) Date of Patent: *Sep. 28, 2010

(54) PROCESS FOR AMPLIFYING NUCLEIC ACID

(75) Inventors: Yasumasa Mitani, Hiroshima-Ken (JP);
Akio Yamane, Hiroshima-Ken (JP);
Yuko Shibata, Kanagawa (JP);
Yoshihide Hayashizaki, Ibaraki-Ken (JP)

(73) Assignees: Riken, Saitama (JP); Kabushiki Kaisha Dnaform, Kanagawa (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/532,975

(22) PCT Filed: Oct. 29, 2003

(86) PCT No.: PCT/JP03/13856
§ 371 (c)(1),
(2), (4) Date: Apr. 28, 2005

(87) PCT Pub. No.: WO2004/040019
PCT Pub. Date: May 13, 2004

(65) Prior Publication Data
US 2006/0160084 A1    Jul. 20, 2006

(30) Foreign Application Priority Data
Oct. 29, 2002 (JP) ............................ 2002-314776

(51) Int. Cl.
C12P 19/34 (2006.01)
C12Q 1/68 (2006.01)
C07H 21/04 (2006.01)

(52) U.S. Cl. ................... 435/91.2; 435/6; 435/91.5; 536/24.33

(58) Field of Classification Search .................. None
See application file for complete search history.

(56) References Cited

U.S. PATENT DOCUMENTS

| | | | |
|---|---|---|---|
| 5,468,613 A | 11/1995 | Erlich et al. | |
| 5,712,124 A | 1/1998 | Walker | |
| 6,063,572 A | 5/2000 | Ishiguro et al. | |
| 6,410,278 B1 | 6/2002 | Notomi et al. | |
| 6,974,670 B2 | 12/2005 | Notomi et al. | |
| 7,175,985 B1 | 2/2007 | Kanda et al. | |
| 2002/0168676 A1 | 11/2002 | Notomi et al. | |
| 2003/0129632 A1 | 7/2003 | Mori et al. | |
| 2004/0038253 A1 | 2/2004 | Nagamine | |
| 2004/0132144 A1 | 7/2004 | Notomi et al. | |
| 2007/0190531 A1 | 8/2007 | Mitani et al. | |
| 2007/0238113 A1 | 10/2007 | Kanda et al. | |

FOREIGN PATENT DOCUMENTS

| | | |
|---|---|---|
| EP | 0 519 338 A1 | 12/1992 |
| EP | 0 648 280 B1 | 5/1999 |
| EP | 1 020 534 A1 | 7/2000 |
| EP | 0 971 039 A2 | 12/2000 |
| EP | 0 754 240 B1 | 8/2003 |
| EP | 0 576 558 B1 | 12/2004 |
| EP | 0 726 905 B1 | 3/2005 |
| JP | 2-5015232 A | 5/1990 |
| JP | 5-192195 A | 8/1993 |
| JP | 10-201476 A | 8/1998 |
| JP | 11-509406 | 8/1999 |
| JP | 2000-37194 A | 2/2000 |
| JP | 2001-503973 A | 3/2001 |
| JP | 3152927 B2 | 4/2001 |
| JP | 2001-161486 | 5/2001 |
| JP | 2002-186481 | 7/2002 |
| JP | 3-313358 B2 | 12/2002 |
| JP | 2002-345499 A | 12/2002 |
| JP | 3897805 | 1/2007 |
| WO | WO 89/01050 A1 | 2/1989 |

(Continued)

OTHER PUBLICATIONS

Notomi et al. Loop-mediated isothermal amplification of DNA. Nucleic Acids Research (2000) 28(12): e63 (7 printed pages).*
Kool, E.T. Synthetically modified DNAs as substrates for polymerases. Current Opinion in Chemical Biology (2000) 4: 602-608.*
Iwamoto et al. Loop-Mediated Isothermal Amplification for Direct Detection of Mycobacterium tuberculosis Complex, M. avium, and M. intracellulare in Sputum Samples. Journal of Clinical Microbiology (2003) 41(6): 2616-2622.*
"Supplemental Partial European Search Report" European Patent Office. Dated May 30, 2007.
Nagamine, K. et al. "Accelerateed Reaction by Loop Mediated Isothermal Amplification Using Loop Primers." Molecular and Cellular Probes, 16 (2002) 223-229.
Walker, G.T. et al. "Strand Displacement Amplification—an Isothermal, in vitro DNA Amplification Technique." Nucleic Acids Research 20:7 (1992) 1691-1696.

(Continued)

Primary Examiner—Kenneth R. Horlick
Assistant Examiner—Angela M Bertagna
(74) Attorney, Agent, or Firm—Hamre, Schumann, Mueller & Larson, P.C.

(57) ABSTRACT

The present invention relates to a process for synthesizing or amplifying efficiently a nucleic acid comprising a target nucleic acid sequence. The process involves providing a primer comprising in its 3'-end portion a sequence (Ac') which hybridizes a sequence (A) in the 3'-end portion of the target nucleic acid sequence, and in the 5'-side of the sequence (Ac') a sequence (B') which hybridizes the complementary sequence (Bc) of a sequence (B) positioned in the 5'-side of the sequence (A) on the target nucleic acid sequence, wherein $\{X-(Y-Y')\}/X$ is in the range of $-1.00$ to $1.00$, in which X denotes the number of bases in the sequence (Ac'), Y denotes the number of bases in the region flanked by the sequences (A) and (B) in the target nucleic acid sequence, and Y' denotes the number of bases in an intervening sequence between the sequences (Ac') and (B') (Y' may be zero).

16 Claims, 14 Drawing Sheets

FOREIGN PATENT DOCUMENTS

| | | |
|---|---|---|
| WO | WO 90/06995 A1 | 6/1990 |
| WO | 91/13075 | 9/1991 |
| WO | 92/15712 | 9/1992 |
| WO | 95/12607 | 5/1995 |
| WO | 95/21271 | 8/1995 |
| WO | WO 96/1327 A1 | 1/1996 |
| WO | 97/00330 | 1/1997 |
| WO | 98/02449 | 1/1998 |
| WO | WO 98/14610 A2 | 4/1998 |
| WO | 98/59066 | 12/1998 |
| WO | WO01/77317 | 10/2001 |
| WO | 01/83817 | 11/2001 |
| WO | WO02/16639 | 2/2002 |
| WO | 02/24902 A1 | 3/2002 |
| WO | WO 02/070735 A2 | 9/2002 |

OTHER PUBLICATIONS

Nagamine, Kentaro et al. "Loop-Mediated Isothermal Amplification Reaction Using a Nondenatured Template." Clinical Chamistry 47:9 (2001) 1742-1743.
Notomi et al., Nucleic Acids Research 28(12): E63-e63 (pp. 1-11).
Notice of Trial for invalidation of JP 3-867926, dated May 20, 2008.
DNA sequence of Hepatitis B Virus of EMBL/GenBank/DDBJ database Accession No. Z72478 (Exhibit 2 of Notice of Trial dated May 20, 2008).
Record of Oral Proceeding issued in the Trial Case for Invalidation of corresponding Japanese patent No. 3867926 mailed Jan. 7, 2009 with its partial English translation.
"Third Party Observations on European Patent Application No. 03769966.7 in the name of Riken and Kabushiki Kaisha DNAform." Issued by the European Patent Office Oct. 22, 2008. (EP 03769966.7 corresponds to the present application, U.S. Appl. No. 10//532975).
Partial Oral Proceedings document for Japanese Patent No. 3867926, dispatch date Oct. 27, 2008. (JP Patent 3867926 corresponds to the present application, U.S. Appl. No. 10/532975).
Office Action issued by the Canadian Patent Office in Canadian Application No. 2,504,234 on Dec. 19, 2008. (CA 2,504,234 corresponds to the present U.S. Appl. No. 10/532975).
"Third Party Observations on European Application No. 04807703.6 (EP1712618) in the name of Riken and Kabushiki Kaisha Dnaform" Issued by the European Patent Office Jul. 24, 2008.
Reference Material 1 (Written argument in JP2005-516642 dated Nov. 13, 2006)—5 pages.
Reference Material 2 (Written reply to the request for a trial for invalidation of a patent No. (invalidation) 2008-800091 dated Aug. 4, 2008)—27 pages.
Demandant's Exhibit No. 8 (Newton, et al., "Analysis of any point mutation in DNA. The amplification refractory mutation system (ARMS)", Nucleic Acids Research. vol. 17, No. 7, pp. 2503-2516, 1989).
Demandant's Exhibit No. 9 (Mukai et al, "PCR Frontier", Protein, Nucleic Acid, Enzyme, vol. 31, No. 5, pp. 425-428).

Trial Decision relating to corresponding Japanese Patent No. 3867926 mailed Mar. 26, 2009 with a full English translation (123 pages).
European Office Action issued in corresponding Application No. 04 807 703.6 and mailed Jun. 30, 2009—6 pages.
Reference Material 1 (Written argument in JP2005-516642 dated Nov. 13, 2006)—5 pages.
Reference Material 2 (Written reply to the request for a trial for invalidation of a patent No. (invalidation) 2008-800091 dated Aug. 4, 2008)—27 pages.
Demandant's Exhibit No. 8 (Newton, et al., "Analysis of any point mutation in DNA. The amplification refractory mutation system (ARMS)", Nucleic Acids Research. vol. 17, No. 7, pp. 2503-2516, 1989).
Demandant's Exhibition No. 9 (Mukai et al, "PCR Frontier", Protein, Nucleic Acid, Enzyme, vol. 31, No. 5, pp. 425-428), publication year 1996.
Trial Decision relating to corresponding Japanese Patent No. 3867926 mailed Mar. 26, 2009 with a full English translation (123 pages).
Nollau, et al., "Methods for detection of point mutations: performance and quality assessment", Clinical Chemistry vol. 43, No. 7, pp. 1114-1128, 1997.
European Office Action issued in corresponding European Application No. 04807703.6, Mar. 10, 2010—5 pages.
Second Canadian Office Action mailed Jul. 6, 2009 in Canadian Patent Application No. 2,504,234 and the response to the Office Action filed Jan. 6, 2010 (43 pages).
Third Canadian Office Action mailed Jan. 19, 2010 in Canadian Patent Application No. 2,504,234 (2 pages).
First Taiwanese Office Action mailed Nov. 11, 2009 in Taiwanese Patent Application No. 93140528 and its concise English explanation (5 pages).
Third Party Observations on European Application No. 04807703.6 (EP 1712618) in the name of RIKEN and Kabushiki Kaisha Dnaform dated Apr. 26, 2010—5 pages.
Examiner S. K. Mummert, U.S. Office Action issued in co-pending U.S. Appl. No. 10/583,706, mailed Mar. 17, 2010—29 pages.
Pastinen, et al., "Minisequencing: A Specific Tool for DNA Analysis and Diagnostics on Oligonucleotide Arrays", Genome Research, vol. 7, 1997, pp. 606-614.
Demandant's Exhibit No. 19 - Sekiya, et al., "Recent Advances in PCR Methodology: Basic Methodology and its Application", Kyoritsu Shuppan Co., Ltd., Jun. 15, 1997, p. 437, right column, lines 5 to 9 and p. 438, right column, the last line to p. 439, left column, line 8, with an English translation.
Second Office Action in European Patent Application No. 03769966.7 corresponding to U.S. Appl. No. 10/532,975, mailed Jun. 24, 2010, 6 pages.
Demandant's 7th Brief for H21 (Gyo-Ke) 10107 (suit for cancelling trial decision of Mukou 2008-800091 [invalidation trial case of JP 3867926 corresponding to U.S. Appl. No. 10/532,975] along with a concise English explanation, 17 pages, Jul. 7, 2010.

* cited by examiner 21 gctacgggtctcgaataaaaatatatggaatggaatgcaatgaatcgaatgtcatagaatgtaatgcaa

3'-END REGION COMMON TO RESPECTIVE SENSE PRIMERS → sY160Lp13 PRIMER 5'-END REGION
sY160Lp16 PRIMER 5'-END REGION 101 tgcaaaaacatggaatccaaatcattgactgaaaggctggtgtcgaaggaattgactccaatggaatcgaa 181 tggaatggaagtgaatgaatagaatcgaactaaatcgaatggaatggaaaggaatggaaggaatgcaatgatt sY160Rp13 PRIMER 5'-END REGION
sY160Rp16 PRIMER 5'-END REGION

← 3'-END REGION COMMON TO RESPECTIVE REVERSE PRIMERS

FIG. 3

LANE 1: DNA SIZE MARKER (pUC19-HpaII)
LANE 2: AMPLIFICATION PRODUCTS OF HUMAN STS DYS237
TREATED WITH RESTRICTION ENZYMES

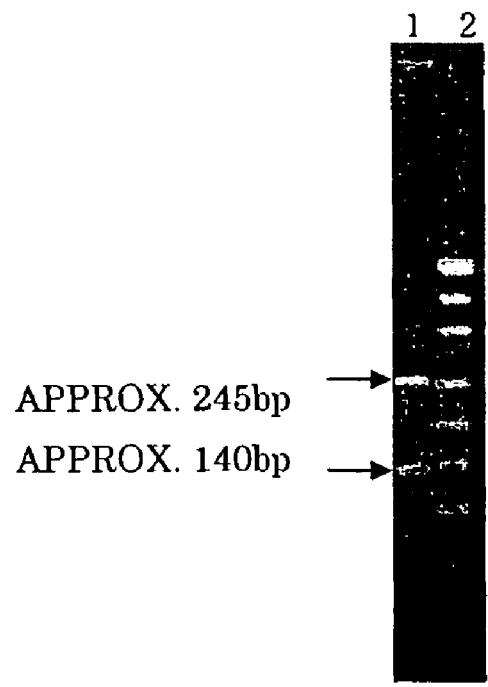
LANE 1: AMPLIFICATION PRODUCTS OF sY160 TREATED
         WITH RESTRICTION ENZYMES
LANE 2: DNA SIZE MARKER (pUC19-HpaII)
F I G. 12

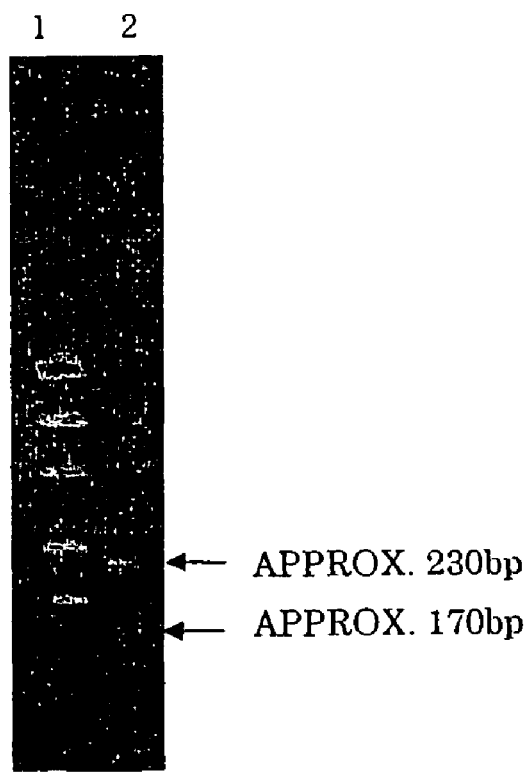
LANE 1: DNA SIZE MARKER (pUC19-HpaII)
LANE 2: AMPLIFICATION PRODUCTS OF M13mp18 TREATED WITH RESTRICTION ENZYMES
F I G. 13

SEQUENCE LISTING

<160> NUMBER OF SEQ ID NOS: 43

<210> SEQ ID NO 1
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 1
gcatcctcat tttatgtcca                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caacccaaaa gcactgagta                                                    20

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagtctctga tgtgcatcct cattttatgt cca                                     33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
agaactcgct ttacaaccca aaagcactga gta                                     33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtattaagtc tctgcatcct cattttatgt cca                                     33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cactaagaac tcgcaaccca aaagcactga gta                                     33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 7
gttcagtatt aaggcatcct cattttatgt cca                                       33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agcatcacta agacaaccca aaagcactga gta                                       33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
catttgttca gtagcatcct cattttatgt cca                                       33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cttgcagcat caccaaccca aaagcactga gta                                       33

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggcatttgtt gcatcctcat tttatgtcca                                           30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcttgcagc caacccaaaa gcactgagta                                           30

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 13
tgtggcattt gttgcatcct cattttatgt cca                                      33

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aacatcttgc agccaaccca aaagcactga gta                                      33

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttatgtggca tttgttgcat cctcatttta tgtcca                                   36

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cttaacatct tgcagccaac ccaaaagcac tgagta                                   36

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttacctttat gtggcatttg ttgcatcctc attttatgtc ca                            42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atttaactta acatcttgca gccaacccaa aagcactgag ta                            42

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcattacctt tatgtggcat ttgttgcatc ctcattttat gtcca                45

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aagatttaac ttaacatctt gcagccaacc caaaagcact gagta                45

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cagtcattac ctttatgtgg catttgttgc atcctcattt tatgtcca             48

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aagaagattt aacttaacat cttgcagcca acccaaaagc actgagta             48

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
attcgattcc gtttacgggt ctcgaatgga ata                             33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctaaatcgaa tggtcattgc attcctttcc att                             33

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
gacattcgat tccgtttacg ggtctcgaat ggaata                                  36
```

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gaactaaatc gaatggtcat tgcattcctt tccatt                                  36
```

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
cgactctaga ggatccccgg gtactgttgt gtggaattgt gagcggat                     48
```

<210> SEQ ID NO 28
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
acaacgtcgt gactgggaaa accctgtgcg ggcctcttcg ctattac                      47
```

<210> SEQ ID NO 29
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
gtgtgaaatt gtttgttgtg tggaattgtg agcggat                                 37
```

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
ttcgccagct ggcgtgcggg cctcttcgct attac                                   35
```

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttcctgtgt gaatgttgtg tggaattgtg agcggat 37

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32 cccccttcg ccagtgcggg cctcttcgct attac 35

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tagctgtttc ctgtgttgtg tggaattgtg agcggat 37

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcacatccc cctgtgcggg cctcttcgct attac 35

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tggtcatagc tgttgttgtg tggaattgtg agcggat 37

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccttgcagca catgtgcggg cctcttcgct attac 35

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
taatcatggt cattgttgtg tggaattgtg agcggat 37

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcgccttgca gcagtgcggg cctcttcgct attac                                35

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctcgaattcg taatcatggt cattgttgtg tggaattgtg agcggat                   47

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cccaacttaa tcgccttgca gcagtgcggg cctcttcgct attac                     45

<210> SEQ ID NO 41
<211> LENGTH: 140
<212> TYPE: DNA
<213> ORGANISM: Homo sapiens

<400> SEQUENCE: 41
agcatcctca ttttatgtcc aacatcagag acttaatact gaacaaatgc cacataaagg     60
taatgactgt tgaagaagat ttaacttaac atcttgcagc atcactaaga actcgcttta   120
tactcagtgc ttttgggttg                                               140

<210> SEQ ID NO 42
<211> LENGTH: 240
<212> TYPE: DNA
<213> ORGANISM: Homo sapiens
<220> FEATURE:
<221> NAME/KEY: modified_base
<222> LOCATION: (48)
<223> OTHER INFORMATION: a, c, t, g, unknown or other

<400> SEQUENCE: 42
gctacgggtc tcgaatggaa taaaatata tggaatggaa tgcaatgnaa cggaatcgaa      60
tgtcatagaa tgtaatgcaa tgcaaaaaca tggaatccaa aatcattgac tggaaaggct   120
gggtgtcgaa aggaattgac tccaatggaa tggaatcgaa tggaatggaa gtgaatagaa   180
tcgaactaaa tcgaatggaa tggaattgat aggaacggaa tggaaaggaa tgcaatgatt   240

<210> SEQ ID NO 43
<211> LENGTH: 300
<212> TYPE: DNA
<213> ORGANISM: Artificial Sequence -continued

```
<220> FEATURE:
<223> OTHER INFORMATION: Description of Artificial Sequence: Synthetic
      phage vector sequence

<400> SEQUENCE: 43
cactcattag gcaccccagg ctttacactt tatgcttccg gctcgtatgt tgtgtggaat        60
tgtgagcgga taacaatttc acacaggaaa cagctatgac catgattacg aattcgagct      120
cggtacccgg ggatcctcta gagtcgacct gcaggcatgc aagcttggca ctggccgtcg      180
ttttacaacg tcgtgactgg gaaaaccctg gcgttaccca acttaatcgc cttgcagcac      240 atccccctttt cgccagctgg cgtaatagcg aagaggcccg caccgatcgc ccttcccaac      300
```

PROCESS FOR AMPLIFYING NUCLEIC ACID

This application is a national stage of PCT/JP03/13856 filed Oct. 29, 2003. The entire contents of the above-identified application are hereby incorporated by reference.

BACKGROUND OF THE INVENTION

1. Field of the Invention

The present invention relates to a process for synthesizing a nucleic acid sequence, which is useful in the field of genetic engineering, as well as a process for amplifying it. More particularly, the present invention relates to a process for synthesizing a nucleic acid sequence with use of strand displacement reaction, and to a process for amplifying it.

2. Background Art

In the field of genetic engineering, there is known an assay based on the complementation of nucleic acids as a method which is capable of directly analyzing genetic features. In such assay, if an aimed gene is present only in a small amount in a sample, it is necessary to previously amplify the aimed gene itself generally due to the difficulty of its detection.

The amplification of the aimed gene (amplification of nucleic acid) is primarily carried out by enzymatic methods with use of DNA polymerase. Such enzymatic methods include, for example, the polymerase chain reaction method (PCR method; U.S. Pat. Nos. 4,683,195, 4,683,202 and 4,800,159), and the reverse transcription PCR method which is the combination of the PCR method and the reverse transcriptase method (RT-PCR method; Trends in Biotechnology, 10, 146-152, 1992). These methods is intended to make capable of amplifying the aimed gene from DNA or RNA by repeating the three step reactions of the dissociation (denaturation) of a double-stranded nucleic acid as a template into a single-stranded nucleic acid, the annealing of a primer to the single-stranded nucleic acid and the synthesis (extension) of a complementary strand from a primer. These methods require the repetition of three steps in total in which the reaction solution is adjusted to a temperature suitable for each reaction in the three steps described above.

There is known the shuttle PCR method as an improvement in the amplification method of nucleic acids described above ("Recent Trends of the PCR method", TANPAKUSHITSU KAKUSAN KOSO (Proteins, Nucleic Acids and Enzymes), KYORITSU SHUPPAN CO., LTD., Vol. 41(5), 425-428 (1996)). In the shuttle PCR method, two steps of the annealing of a primer and the extension among the three-step reactions in the PCR method are carried out at the same temperature, so that the aimed gene can be amplified by the reactions of two steps in total. Furthermore, EP Laid-Open Publication No. 0320308 discloses the ligase chain reaction method (LCR method), in which a known gene sequence is amplified by two-step temperature cycling (repeated reactions with heating and cooling).

In the methods described above, it is necessary to use a thermal cycler which can control temperature strictly in an extensive range. In addition, these reactions are carried out at two or three temperature conditions and require time for adjusting respective reaction temperatures, so that the more increased the cycles, the longer the time required for it.

In order to solve the aforementioned problems, methods for amplifying nucleic acids which can be conducted under an isothermal condition have been developed. Such methods include, for example, the strand displacement amplification (SDA) method and the self-sustained sequence replication (3SR) method described in Japanese Patent Publication No. 7/114718, the nucleic acid sequence based amplification (NASBA) method and the transcription-mediated amplification (TMA) method described in Japanese Patent No. 2650159, the Q beta replicase method described in Japanese Patent No. 2710159, a variety of the improved SDA methods described in U.S. Pat. No. 5,824,517, International Publications WO99/09211 or WO95/25180, the LAMP (Loop-Mediated Isothermal Amplification) method described in International Publication WO00/28082, the ICAN (Isothermal and Chimeric primer-initiated Amplification of Nucleic acids) method described in International Publication WO02/16639, and the like. The reactions of all steps involved in the isothermal amplification of nucleic acids proceed simultaneously in reaction mixtures maintained at a constant temperature.

In the SDA method, it is possible to amplify the aimed nucleic acid (and its complementary strand) in a sample by the displacement of a double strand mediated by DNA polymerases and restriction endonucleases. This method involves four primers, of which the two primers must be designed to include the recognition sites of the restriction endonucleases. In addition, this method requires as a substrate for the synthesis of nucleic acids modified deoxynucleotide triphosphates such as a deoxynucleotide triphosphate in which the oxygen atom of the phosphate group at the alpha-position of the triphosphate moiety has been substituted by a sulfur atom (S). This method requires high running cost. Furthermore, in this method, modified nucleotides such as alpha-S-displaced deoxynucleotides are included in the amplified nucleic acid fragment, so that when the amplified fragment is subjected to the restriction enzyme fragment length polymorphism (RFLP) assay, it cannot be broken with the restriction enzyme and thus such assay cannot be practiced in some cases.

The SDA method described in U.S. Pat. No. 5,824,517 requires a chimeric primer comprising RNA and DNA, in which DNA is in the 3'-end side. Such chimeric primer composed of RNA and DNA requires high cost of its synthesis, and RNA containing primers also require professional knowledge for its handling. In addition, the improved SDA method described in International Publication WO99/09211 requires a restriction enzyme which generates a 5'-protruding end, and the improved SDA method described in International Publication WO95/25180 requires at least two primer pairs, so that these methods also require high running cost.

The ICAN method requires a chimeric primer comprising RNA and DNA, in which RNA is in the 3'-end side, and an RNase H for cutting the RNA moiety at the 3'-end of the primer, so that reagents required for the method cost a great deal. Thus, this method requires high running cost particularly in genetic tests on a large amount of samples.

The LAMP method requires four primers, which recognize six regions to amplify the aimed genes. That is, in this method, the first primer anneals a template strand to cause extension, and a stem-loop structure is formed at the 5'-end portion of the extended strand due to the constitution of the first primer. The extended strand is next separated from the template strand by the strand displacement reaction of the second primer which is designed in the upper-stream of the first primer. Similar reactions occur repeatedly also on the other strand of the double-stranded nucleic acid, and thus the target nucleic acid is amplified. Therefore, the mechanism of the amplification reactions is complicated, and the six regions must be selected, so that it becomes difficult to design primers. In addition, the two of four primers are required to be comparatively long chain primers, and thus the synthesis and purification of the primers is expensive and takes a lot of time.

Therefore, there is a need for a process for amplifying nucleic acids, which can be practiced with a low running cost and the nucleic acid fragment thus obtained can be further used for genetic engineering treatments. Particularly, it is desired to have an isothermal nucleic acid amplification method in which amplification can be conducted quickly with a pair of primers.

SUMMARY OF THE INVENTION

The present inventors have found that a nucleic acid having a nucleic acid sequence complementary to a target nucleic acid sequence can be synthesized by using a primer designed in such a way that it is capable of forming a stem-loop structure by the extension of the primer and satisfies additional specific requirements, and that a target nucleic acid can be amplified efficiently by using two such primers. The present invention is based on these findings.

Accordingly, it is an object of the present invention to provide a process for synthesizing or amplifying efficiently a nucleic acid having a target nucleic acid sequence, as well as a primer and a primer set for use therein.

The process for synthesizing a nucleic acid according to the present invention is a process. for synthesizing a nucleic acid complementary to a target nucleic acid sequence in a template nucleic acid, which comprises the steps of:
(a) providing a primer comprising in its 3'-end portion a sequence (Ac') which hybridizes a sequence (A) in the 3'-end portion of the target nucleic acid sequence, and in the 5'-side of said sequence (Ac') a sequence (B') which hybridizes the complementary sequence (Bc) of a sequence (B) positioned in the 5'-side of said sequence (A) on the target nucleic acid sequence, wherein
in the absence of an intervening sequence between said sequences (Ac') and (B'), (X−Y)/X is in the range of −1.00 to 1.00, in which X denotes the number of bases in said sequence (Ac'), and Y denotes the number of bases in the region flanked by said sequences (A) and (B) on the target nucleic acid sequence, and
in the presence of an intervening sequence between said sequences (Ac') and (B'), {X−(Y−Y')}/X is in the range of −1.00 to 1.00, in which X and Y have the same meanings as above, and Y' denotes the number of bases in said intervening sequence;
(b) providing a template nucleic acid;
(c) annealing said primer to said template nucleic acid and synthesizing a complementary nucleic acid comprising the complementary sequence of said target nucleic acid sequence by primer extension reaction;
(d) hybridizing the sequence (B') positioned in the 5'-side of the complementary nucleic acid synthesized in the step (c) with the sequence (Bc) on the same complementary nucleic acid, thereby allowing the portion of said sequence (A) on the template nucleic acid to be single-stranded; and
(e) annealing another primer having the same sequence as said primer to the single-stranded sequence (A) portion of the template nucleic acid from the step (d) and conducting strand displacement reaction, thereby displacing the complementary nucleic acid synthesized in the step (c) by the complementary nucleic acid newly synthesized with said another primer.

The process for amplifying a nucleic acid according to the present invention is a process for amplifying a target nucleic acid sequence in a double stranded template nucleic acid, which comprises the steps of:
(a) providing a first primer comprising in its 3'-end portion a sequence (Ac') which hybridizes a sequence (A) in the 3'-end portion of the target nucleic acid sequence in the first strand of the double-stranded template nucleic acid, and in the 5'-side of said sequence (Ac') a sequence (B') which hybridizes the complementary sequence (Bc) of a sequence (B) positioned in the 5'-side of said sequence (A) on said target nucleic acid sequence, wherein
in the absence of an intervening sequence between said sequences (Ac') and (B'), (X−Y)/X is in the range of −1.00 to 1.00, in which X denotes the number of bases in said sequence (Ac'), and Y denotes the number of bases in the region flanked by said sequences (A) and (B) on the target nucleic acid sequence, and
in the presence of an intervening sequence between said sequences (Ac') and (B'), {X−(Y−Y')}/X is in the range of −1.00 to 1.00, in which X and Y have the same meanings as above, and Y' denotes the number of bases in said intervening sequences;
(b) providing a second primer comprising in its 3'-end portion a sequence (Cc') which hybridizes a sequence (C) in the 3'-end portion of the target nucleic acid sequence in the second strand of the double-stranded template nucleic acid, and in the 5'-side of said sequence (Cc') a sequence (D') which hybridizes the complementary sequence (Dc) of a sequence (D) positioned in the 5'-side of said sequence (C) on said target nucleic acid sequence, wherein
in the absence of an intervening sequence between said sequences (Cc') and (D'), (X−Y)/X is in the range of −1.00 to 1.00, in which X denotes the number of bases in said sequence (Cc'), and Y denotes the number of bases in the region flanked by said sequences (C) and (D) on the target nucleic acid sequence, and
in the presence of an intervening sequence between said sequences (Cc') and (D'), {X−(Y−Y')}/X is in the range of −1.00 to 1.00, in which X and Y have the same meanings as above, and Y' denotes the number of bases in said intervening sequence;
(c) providing a double stranded template nucleic acid consisting of the first and second template nucleic acids;
(d) annealing said first and second primers to said first and second template nucleic acids, respectively, and synthesizing the first and second complementary nucleic acids comprising the complementary sequence of said target nucleic acid by the primer extension reaction, respectively;
(e) hybridizing the sequences (B') and (D') positioned in the 5'-side of the first and second complementary nucleic acids synthesized in the step (d) with the sequences (Bc) and (Dc) on the same complementary nucleic acids, respectively, and thereby allowing the portions of said sequences (A) and (C) on the first and second template nucleic acids to be single-stranded, respectively; and
(f) annealing another primers having the same sequence as said primers to the single-stranded sequence (A) and (C) portions of the first and second template nucleic acids from the step (e) and conducting strand displacement reaction, thereby displacing the first and second complementary nucleic acids synthesized in the step (d) by the complementary nucleic acids newly synthesized with said another primers.

Furthermore, the primer according to the present invention is a primer for synthesizing a nucleic acid complementary to a target nucleic acid sequence in a template nucleic acid, comprising in its 3'-end portion a sequence (Ac') which hybridizes a sequence (A) in the 3'-end portion of the target nucleic acid sequence, and in the 5'-side of said sequence (Ac') a sequence (B') which hybridizes the complementary sequence (Bc) of a sequence (B) positioned in the 5'-side of said sequence (A) on the target nucleic acid sequence, wherein in the absence of an intervening sequence between said sequences (Ac') and (B'), (X−Y)/X is in the range of −1.00 to 1.00, in which X denotes the number of bases in said sequence (Ac'), and Y denotes the number of bases in the region flanked by said sequences (A) and (B) on the target nucleic acid sequence, and in the presence of an intervening sequence between said sequences (Ac') and (B'), {X−(Y−Y')}/X is in the range of −1.00 to 1.00, in which X and Y have the same meanings as above, and Y' denotes the number of bases in said intervening sequence.

The primer set according to the present invention is a primer set for amplifying a target nucleic acid sequence in a double-stranded template nucleic acid, which comprises:

(a) a first primer comprising in its 3'-end portion a sequence (Ac') which hybridizes a sequence (A) in the 3'-end portion of the target nucleic acid sequence in the first strand of the double-stranded template nucleic acid, and in the 5'-side of said sequence (Ac') a sequence (B') which hybridizes the complementary sequence (Bc) of a sequence (B) positioned in the 5'-side of said sequence (A) on said target nucleic acid sequence, wherein in the absence of an intervening sequence between said sequences (Ac') and (B'), (X−Y)/X is in the range of −1.00 to 1.00, in which X denotes the number of bases in said sequence (Ac'), and Y denotes the number of bases in the region flanked by said sequences (A) and (B) on the target nucleic acid sequence, and in the presence of an intervening sequence between said sequences (Ac') and (B'), {X−(Y−Y')}/X is in the range of −1.00 to 1.00, in which X and Y have the same meanings as above, and Y' denotes the number of bases in said intervening sequence; and (b) a second primer comprising in its 3'-end portion a sequence (Cc') which hybridizes a sequence (C) in the 3'-end portion of the target nucleic acid sequence in the second strand of the double-stranded template nucleic acid, and in the 5'-side of said sequence (Cc') a sequence (D') which hybridizes the complementary sequence (Dc) of a sequence (D) positioned in the 5'-side of said sequence (C) on said target nucleic acid sequence, wherein in the absence of an intervening sequence between said sequences (Cc') and (D'), (X−Y)/X is in the range of −1.00 to 1.00, in which X denotes the number of bases in said sequence (Cc'), and Y denotes the number of bases in the region flanked by said sequences (C) and (D) on the target nucleic acid sequence, and in the presence of an intervening sequence between said sequences (Cc') and (D'), {X−(Y−Y')}/X is in the range of −1.00 to 1.00, in which X and Y have the same meanings as above, and Y' denotes the number of bases in said intervening sequence.

According to the present invention, it is possible to synthesize continuously the target DNA under an isothermal condition by using DNA or RNA as a template and an oligonucleotide primer. According to the present invention, it is also possible to amplify continuously the target DNA under an isothermal condition by using DNA or RNA as a template and a pair of oligonucleotide primers. Thus, the process according to the present invention requires no special apparatuses such as a thermal cycler and no time for the setting of temperature, and thus exhibits an excellent effect that amplified products can be obtained in a short time. Moreover, the DNA fragment amplified according to the present invention can be treated with restriction enzymes and thus can be employed in the field of genetic tests such as restriction enzyme fragment length polymorphism or detection of mutation.

BRIEF DESCRIPTION OF THE DRAWINGS

FIG. 3 shows the positions of a primer used for the amplification of an sY160 gene in the 5'-side and 3'-side (SEQ ID NO: 42).

FIG. 12 shows electrophoresis patterns obtained by the treatment of an amplification product from an sY160 gene with restriction enzymes.

FIG. 13 shows electrophoresis patterns obtained by the treatment of an amplification product from an M13mp18RT DNA with restriction enzymes.

DETAILED DESCRIPTION OF THE INVENTION

Figure 1:
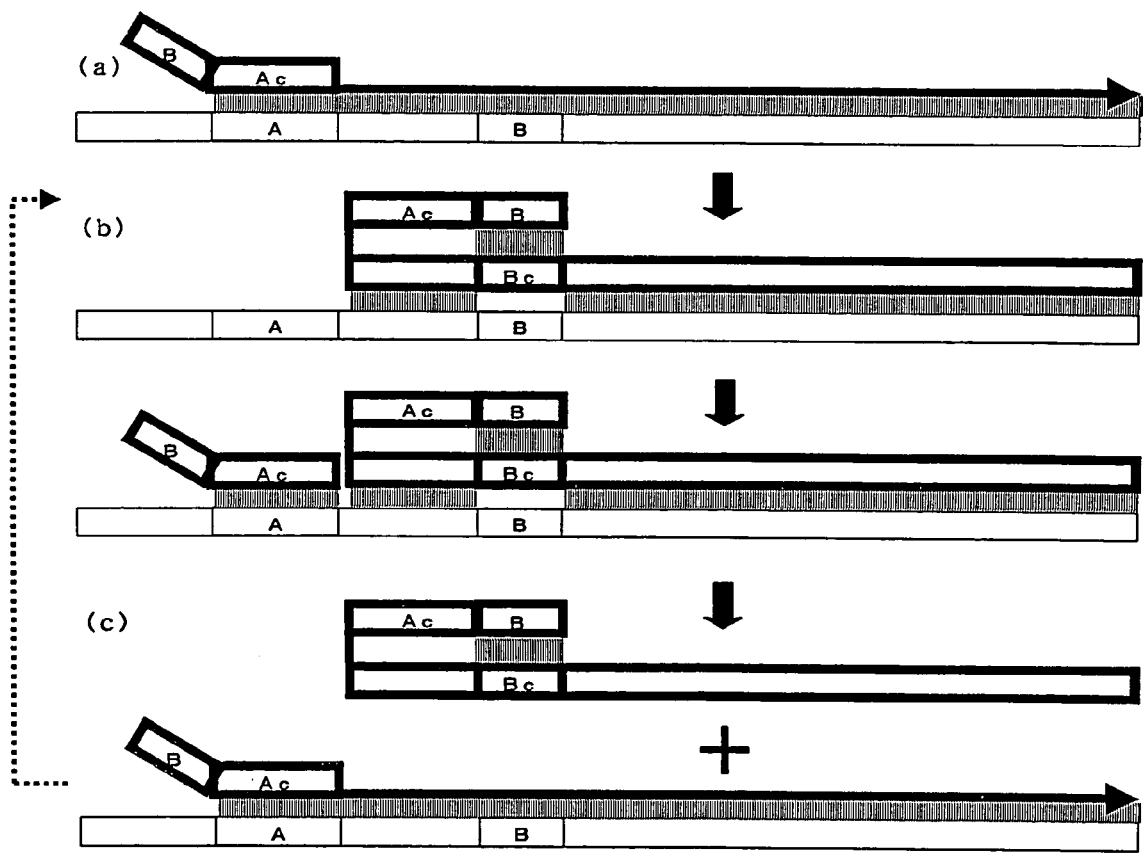
FIG. 1 shows the schematic diagram of the process for amplifying nucleic acids according to the present invention.

The mechanism of the synthesis of a nucleic acid according to the present invention is schematically illustrated in FIG. 1. First, the sequence of a target nucleic acid in a nucleic acid as a template is determined, and then the sequence (A) of the 3'-end portion and the sequence (B) positioned in the 5'-side of said sequence (A) on the target nucleic acid sequence are determined. The primer according to the invention comprises a sequence (Ac'), and further comprises a sequence (B') in the 5'-side thereof. The sequence (Ac') hybridizes the sequence (A). The sequence (B') hybridizes the complementary sequence (Bc) of the sequence (B). In this connection, the primer according to the present invention may comprise an intervening sequence between said sequences (Ac') and (B'), the intervening sequence per se having no influence on the reaction. The annealing of the primer to a template nucleic acid will result in a state in which sequence (Ac') in the primer has hybridized the sequence (A) of the target nucleic acid (FIG. 1(a)). A nucleic acid comprising the complementary sequence of the target nucleic acid is synthesized by the primer extension reaction in this state. Then, the sequence (B') positioned in the 5'-end side of the nucleic Bacid thus synthesized hybridizes the sequence in the same nucleic acid to form a stem-loop structure in the 5'-end side of the synthesized nucleic acid. As a result thereof, the sequence (A) on the template nucleic acid becomes a single strand, to which another primer having the same sequence as the previous primer hybridizes (FIG. 1(b)). The nucleic acid synthesized previously is then separated from the template nucleic acid at the same time as the extension reaction from the newly hybridized primer by the strand displacement reaction (FIG. 1(c)).

In the aforementioned reaction mechanism, the phenomenon of the hybridization of the sequence (B') to the sequence (Bc) is caused by the presence of a complementary region on the same strand. Generally, the dissociation of a double-stranded nucleic acid to single strands begins from a comparatively unstable part such as its terminal or the like. The double-stranded nucleic acid produced by the extension reaction with the primer described above is in an equilibrium state between the dissociation and bonding of a base pair in the terminal moiety at comparatively high temperature and maintains a double strand as a whole. If a strand complementary to the dissociated terminal moiety in such situation is present in the same strand, a stem-loop structure can be formed as a metastable state. While such stem-loop structure is not present stably, the same primer immediately binds to the sequence (A) on the template nucleic acid as the complementary strand moiety which has been exposed by the formation of the structure, and the extension reaction with a polymerase causes the liberation of the previously synthesized strand and the production of a new double-stranded nucleic acid at the same time.

By repeating the reactions described above, it is possible to synthesize a nucleic acid complementary to the sequence of the target nucleic acid in the template nucleic acid in a large amount. It is also possible to synthesize nucleic acids in the same manner with a complementary strand of the template nucleic acid described above as a template. Thus, it is possible to amplify the target nucleic acid in the double-stranded template nucleic acid according to the invention.

The process for synthesizing a nucleic acid according to the invention comprises the steps of:

(a) providing a primer comprising in its 3'-end portion a sequence (Ac') which hybridizes a sequence (A) in the 3'-end portion of the target nucleic acid sequence, and in the 5'-side of said sequence (Ac') a sequence (B') which hybridizes the complementary sequence (Bc) of a sequence (B) positioned in the 5'-side of said sequence (A) on the target nucleic acid sequence, wherein
in the absence of an intervening sequence between said sequences (Ac') and (B'), (X−Y)/X is in the range of −1.00 to 1.00, in which X denotes the number of bases in said sequence (Ac'), and Y denotes the number of bases in the region flanked by said sequences (A) and (B) on the target nucleic acid sequence, and
in the presence of an intervening sequence between said sequences (Ac') and (B'), {X−(Y−Y')}/X is in the range of −1.00 to 1.00, in which X and Y have the same meanings as above, and Y' denotes the number of bases in said intervening sequence;
(b) providing a template nucleic acid;
(c) annealing said primer to said template nucleic acid and synthesizing a complementary nucleic acid comprising the complementary sequence of said target nucleic acid sequence by primer extension reaction;
(d) hybridizing the sequence (B') positioned in the 5'-side of the complementary nucleic acid synthesized in the step (c) with the sequence (Bc) on the same complementary nucleic acid, thereby allowing the portion of said sequence (A) on the template nucleic acid to be single-stranded; and
(e) annealing another primer having the same sequence as said primer to the single-stranded sequence (A) portion of the template nucleic acid from the step (d) and conducting strand displacement reaction, thereby displacing the complementary nucleic acid synthesized in the step (c) by the complementary nucleic acid newly synthesized with said another primer.

The term "hybridize" herein means that a part of a primer according to the invention hybridizes a target nucleic acid under a stringent condition, but not nucleic acids other than the target nucleic acid The stringent condition may be determined depending on factors such as the melting temperatures Tm (° C.) of the double strand of the primer according to the invention and its complementary strand and the salt concentrations of hybridization solutions, and the teachings of the references, such as, for example, J. Sambrook, E. F. Frisch, T. Maniatis; Molecular Cloning 2nd edition, Cold Spring Harbor Laboratory (1989) which is incorporated herein by reference. For example, it is possible to specifically hybridize a primer to a target nucleic acid by hybridization at a little lower temperature than the melting temperature used. Such primer can be designed with commercially available primer construction softwares such as Primer 3 (Whitehead Institute for Biomedical Research). According to the preferred embodiments of the invention, a primer hybridizing a certain target nucleic acid comprises the all or a part of a nucleic acid molecule complementary to the target nucleic acid.

The primer according to the invention provided in the step (a) described above is constructed in such a way that it is capable of annealing to a template nucleic acid in the step (C), and providing the hybridization of the sequences (B) and (Bc) in the step (d) and a single-stranded sequence (A) to which another primer having the same sequence can anneal. The construction of the primers for conducting preferably these steps is described in more details in the following.

In order to conduct efficient annealing of a new primer in the step (e) described above, it is necessary to allow the portion of said sequence (A) on the template nucleic acid to be single-stranded by the formation of the stem-loop structure in the step (d) of the complementary nucleic acid synthesized in the step (c). Thus, it is important to determine (X−Y)/X which is the ratio of the difference (X−Y) to X, in which X denotes the number of bases in said sequence (Ac'), and Y denotes the number of bases in the region flanked by said sequences (A) and (B) in the target nucleic acid sequence. In this connection, it is not necessary to allow also a portion which is positioned in the 5'-side of the sequence (A) on the template nucleic acid and which does not affect the hybridization of the primer to be single-stranded. In addition, the efficient annealing of the new primer in the step (e) described above requires the efficient formation of the stem-loop structure in the step (d) on the complementary nucleic acid synthesized in the step (c). It is also important for the efficient formation of the stem-loop structure, that is, the efficient hybridization of the sequence (B') and the sequence (Bc), to adjust the distance (X+Y) between the sequences (B') and (Bc). Generally, the optimal temperature for the primer extension reaction is up to about 72° C., and thus it is difficult to dissociate the long region of the extended strand at such lower temperature. It is thus believed more preferred for the efficient hybridization of the sequence (B') to the sequence (Bc) to have lesser number of bases between both sequences. On the other hand, it is believed more preferred for the hybridization of the sequence (B') to the sequence (Bc) to allow the portion of the sequence (A) on the template nucleic acid to be single-stranded, to have more number of bases between both sequences.

From the viewpoint described above, in the absence of an intervening sequence between said sequences (Ac') and (B'), the primer according to the invention is designed in such fashion that (X−Y)/X is in the range of −1.00 or more, preferably 0.00 or more, more preferably 0.05 or more, and even more preferably 0.10 or more, and in the range of 1.00 or less, preferably 0.75 or less, more preferably 0.50 or less, and even more preferably 0.25 or less. Moreover, (X+Y) is preferably in the range of 15 or more, more preferably 20 or more, even more preferably 30 or more, and preferably in the range of 50 or less, more preferably 48 or less, and even more preferably 42 or less.

Also, in the presence of an intervening sequence between said sequences (Ac') and (B'), the primer according to the invention is designed in such fashion that {X−(Y−Y')}/X is in the range of −1.00 or more, preferably 0.00 or more, more preferably 0.05 or more, even more preferably 0.10 or more, and in the range of 1.00 or less, preferably 0.75 or less, more preferably 0.50 or less, and even more preferably 0.25 or less. Moreover, (X+Y+Y') is preferably in the range of 15 or more, more preferably 20 or more, even more preferably 30 or more, and preferably in the range of 100 or less, more preferably 75 or less, and even more preferably 50 or less.

The primer according to the invention is composed of deoxynucleotides and/or ribonucleotides, and has a strand length in which base pair bonding with the target nucleic acid can be conducted while required specificity is maintained under the given condition. The primer according to the invention has a strand length in the range of preferably 15-100 nucleotides, and more preferably 30-60 nucleotides. Also, the sequences (Ac') and (B') have the lengths preferably in the range of 5-50 nucleotides, and more preferably 10-30 nucleotides, respectively. If necessary, an intervening sequence having itself no influence on the reaction may be inserted between said sequences (Ac') and (B').

In the present invention, the term "ribonucleotide" (also referred to as merely "N") means a ribonucleotide triphosphate and includes, for example, ATP, UTP, CTP, GTP, and the like. Moreover, the ribonucleotides includes derivatives thereof such as, for example, alpha-thio-ribonucleotides in which the oxygen atom of alpha-position of the phosphate group substituted by a sulfur atom.

In addition, the primers according to the invention include oligonucleotide primers composed of unmodified deoxynucleotides and/or modified deoxynucleotides, as well as oligonucleotide primers composed of unmodified ribonucleotides and/or modified ribonucleotides, chimeric oligonucleotide primers containing unmodified deoxynucleotides and/or modified deoxynucleotides and unmodified ribonucleotides and/or modified ribonucleotides, and the like.

The primers according to the invention can be synthesized by any methods which can be used for the synthesis of oligonucleotides, such as the phosphate triesterification method, the H-phosphonate method, the thiophosphonate method, and the like. The primers according to the invention can be easily obtained by the synthetic methods such as, for example, the phosphoamidite method with use of a DNA synthesizer model 394 (ABI, Applied Biosystem Inc.).

The DNA polymerases used in the process for synthesizing nucleic acids according to the invention may be those having strand displacement activities (strand displacement ability), and either of normal temperature, mesophilic or thermoduric polymerases may be successfully used. Also, the DNA polymerases may be either one of natural products or variants having been artificially varied. Furthermore, the DNA polymerases are preferably those having substantially no 5'→3' exonuclease activities. Such DNA polymerases include, for example, a variant of a DNA polymerase derived from thermophilic bacillus bacteria such as *Bacillus stearothermophilus* (referred to hereinafter as B. st) and *Bacillus caldotenax* (referred to hereinafter as B. ca) of which the 5'→3' exonuclease activity has been deleted, the Klenow fragment of an *E. coli* DNA polymerase I, and the like. The DNA polymerases used in the process for synthesizing nucleic acids according to the invention further include Vent DNA polymerase, Vent (Exo-) DNA polymerase, DeepVent DNA polymerase, DeepVent (Exo-) DNA polymerase, φ29 phage DNA polymerase, MS-2 phage DNA polymerase, Z-Taq DNA polymerase, Pfu DNA polymerase, Pfu turbo DNA polymerase, KOD DNA polymerase, 9° Nm DNA polymerase, Therminater DNA polymerase, and the like.

The other reagents which may be used in the process for synthesizing nucleic acids according to the invention include catalysts such as magnesium chloride, magnesium acetate, magnesium sulfate, and the like; substrates such as dNTP mix, and the like; and buffers such as Tris-HCl buffer, Tricine buffer, phosphate Na buffer, phosphate K buffer, and the like. In addition, there may be used additives such as dimethyl sulfoxide, and betaine (N,N,N-trimethylglycine), acidic materials described in International Publication WO99/54455, cationic complexes, and the like.

The nucleic acids used as a template in the process for synthesizing nucleic acids according to the invention may be either DNA or RNA. These nucleic acids can be isolated from samples derived from organisms such as blood, tissues, cells as well as animals or plants, or from microorganisms which have been separated from foodstuffs, soils, drainage, and the like.

The template nucleic acid can be isolated by optional methods including, for example, dissolution treatment with surface active agents, sonification, shaking agitation with glass beads, and a method with a French press. Also, in the presence of endonuclease, it is preferred to purify the nucleic acid isolated. The nucleic acid can be purified by the methods such as for example phenol extraction, chromatography, ion-exchange, gel electrophoresis, density-dependent centrifugation, and the like.

More particularly, it is possible to use either of double-stranded nucleic acids such as a genomic DNA or a PCR fragment isolated by the methods described above or single-stranded nucleic acids such as a cDNA prepared by reverse transcription from whole RNA or mRNA. The double-stranded nucleic acid can be optimally used by forming a single strand by the denaturing of it.

Enzymes used in the reverse transcription reaction are not particularly limited except that the enzymes have a cDNA synthesizing activity from RNA as a template, and include reverse transcriptases derived from a variety of sources such as avian myeloblastosis virus derived reverse transcriptase (AMV RTase), Rous related virus-2 reverse transcriptase (RAV-2 RTase), Moloney murine leukemia virus derived reverse transcriptase (MMLV RTase), and the like. In addition, it is possible to use a DNA polymerase having also a reverse transcription activity. It is also possible to use Thermus bacteria derived DNA polymerase (TthDNA polymerase and the like), Bacillus bacteria derived DNA polymerase, and the like. Particularly preferred enzymes include, for example, thermophilic Bacillus bacteria derived DNA polymerases such as B. st derived DNA polymerase, and B. ca derived DNA polymerases (Bca DNA polymerases) such as Bca-BEST DNA polymerase, Bca (exo-) DNA polymerase, and the like. By way of example, the Bca DNA polymerase requires no manganese ion in the reaction, and it is possible to synthesize cDNA while suppressing the formation of the secondary structure of a template RNA under high temperature conditions.

Furthermore, in the process for synthesizing nucleic acids according to the invention, it is possible to conduct the reverse transcription reaction from whole RNA or mRNA and the DNA polymerase reaction in the presence of CDNA as a template with a polymerase such as BcaBEST DNA polymerase, Bca(exo-) DNA polymerase, and the like. Also, the DNA polymerase may be combined with a reverse transcriptase such as MMLV reverse transcriptase, and the like.

In the process for synthesizing nucleic acids according to the invention, while it is possible to use the template nucleic acid, even if it is a double-stranded nucleic acid, directly in the reaction, it is also possible to carry out efficiently the annealing of a primer to the template nucleic acid after it is denatured into a single strand, if necessary. Heating to about 95° C. is a preferred denaturation method. The other denaturation methods also include the denaturation of nucleic acids by ascending pH, but in this case it is necessary to descend pH in order to hybridize the primer to the target nucleic acid.

According to the preferred embodiment of the present invention, the double-stranded nucleic acid obtained in the step (e) is used repeatedly in the step (d). That is to say, the double-stranded nucleic acid obtained in the step (e) has the same structure as those obtained in the step (c), and thus it is directly used in the step (d). It is thus possible to produce in a large scale a nucleic acid complementary to the target nucleic acid sequence in the template nucleic acid.

One of the features of the process for synthesizing nucleic acids according to the invention is the practicability in an isothermal condition. Thus, according to the invention, there is provided a process for synthesizing a nucleic acid complementary to a target nucleic acid sequence in a template nucleic acid, comprising a step of providing a solution for synthesizing nucleic acids which comprises the template nucleic acid and the primer according to the invention, and a step of isothermally incubating the nucleic acid synthesizing solution. In this connection, the term "isothermally" means that temperature is maintained at about constant temperature so as the enzyme and the primer to be substantially functional.

The process for synthesizing nucleic acids according to the invention can be carried out by maintaining the temperature in the range in which the activity of the enzyme used is maintained. Also, in order to anneal the primer to the target nucleic acid in the process for synthesizing nucleic acids according to the invention, the reaction temperature is preferably set in the vicinity of the melting temperature (Tm) of the primer or less, and the level of stringency is preferably set in view of the melting temperature (Tm) of the primer. Thus, the temperature is preferably in the range of about 20- about 75° C., more preferably in the range of about 35- about 65° C.

In the process for synthesizing nucleic acids according to the invention, it is possible to amplify the target nucleic acid sequence in a double-stranded nucleic acid by using the double-stranded nucleic acid as a template and a primer set comprising the two primers according to the invention designed for each of the strands. Thus, according to the invention, there is provided a process for amplifying a target nucleic acid sequence in a double-stranded template nucleic acid, which comprises the steps of:

(a) providing a first primer comprising in its 3'-end portion a sequence (Ac') which hybridizes a sequence (A) in the 3'-end portion of the target nucleic acid sequence in the first strand of the double-stranded template nucleic acid, and in the 5'-side of said sequence (Ac') a sequence (B') which hybridizes the complementary sequence (Bc) of a sequence (B) positioned in the 5'-side of said sequence (A) on said target nucleic acid sequence, wherein in the absence of an intervening sequence between said sequences (Ac') and (B'), (X−Y)/X is in the range of −1.00 to 1.00, in which X denotes the number of bases in said sequence (Ac'), and Y denotes the number of bases in the region flanked by said sequences (A) and (B) on the target nucleic acid sequence, and in the presence of an intervening sequence between said sequences (Ac') and (B'), {X−(Y−Y')}/X is in the range of −1.00 to 1.00, in which X and Y have the same meanings as above, and Y' denotes the number of bases in said intervening sequence;

(b) providing the second primer comprising in its 3'-end portion a sequence (Cc') which hybridizes a sequence (C) in the 3'-end portion of the target nucleic acid sequence in the second strand of the double-stranded template nucleic acid, and in the 5'-side of said sequence (Cc') a sequence (D') which hybridizes the complementary sequence (Dc) of a sequence (D) positioned in the 5'-side of said sequence (C) on said target nucleic acid sequence, wherein in the absence of an intervening sequence between said sequences (Cc') and (D'), (X−Y)/X is in the range of −1.00 to 1.00, in which X denotes the number of bases in said sequence (Cc'), and Y denotes the number of bases in the region flanked by said sequences (C) and (D) on the target nucleic acid sequence, and in the presence of an intervening sequence between said sequences (Cc') and (D'), {X−(Y−Y')}/X is in the range of −1.00 to 1.00, in which X and Y have the same meanings as above, and Y' denotes the number of bases in said intervening sequence;

(c) providing a double-stranded template nucleic acid consisting of the first and second template nucleic acids;

(d) annealing said first and second primers to said first and second template nucleic acids, respectively, and synthesizing the first and second complementary nucleic acids comprising the complementary sequence of said target nucleic acid by the primer extension reaction, respectively;

(e) hybridizing the sequences (B') and (D') positioned in the 5'-side of the first and second complementary nucleic acids synthesized in the step (d) with the sequences (Bc) and (Dc) on the same complementary nucleic acids, respectively, and thereby allowing the portions of said sequences (A) and (C) on the first and second template nucleic acids to be single-stranded, respectively; and (f) annealing another primers having the same sequence as said primers to the single-stranded sequence (A) and (C) portions of the first and second template nucleic acids from the step (e) and conducting strand displacement reaction, thereby displacing the first and second complementary nucleic acids synthesized in the step (d) by the complementary nucleic acids newly synthesized with said another primers.

In this connection, the details on the design of the primers, the reaction conditions and the like are the same as described above on the process for synthesizing nucleic acids according to the invention.

According to the preferred embodiments of the invention, the double-stranded nucleic acid obtained by the step (f) in the process for amplifying nucleic acids according to the invention is used repeatedly in the step (e). That is to say, the double-stranded nucleic acid obtained by the step (f) has the same structure as those obtained in the step (d), and thus it is directly used in the step (e).

According to the other preferred embodiments, the first and second complementary nucleic acids obtained as single-stranded nucleic acids by the step (f) are used repeatedly as the second and first template nucleic acids, respectively, in the step (d). That is, the first complementary nucleic acid obtained by the step (f) is used as the second template nucleic acid in the step (d), and the second complementary nucleic acid obtained by the step (f) is used as the first template nucleic acid in the step (d).

The process for amplifying nucleic acids according to the invention can be practiced isothermally in the similar manner to the process for synthesizing nucleic acids according to the invention. Thus, according to the invention, there is provided a process for amplifying a target nucleic acid sequence in a double-stranded template nucleic acid, comprising a step of providing a solution for amplifying a nucleic acid which comprises the double-stranded template nucleic acid and the primer set according to the invention, and a step of isothermally incubating the solution for amplifying the nucleic acid. In this connection, the term "isothermally" means that temperature is maintained at about constant temperature so as the enzyme and the primer to be substantially functional. The details on the temperature conditions are the same as described above on the process for synthesizing nucleic acids according to the invention.

The process for amplifying the nucleic acid according to the invention can be carried out optimally as the process for amplifying a nucleic acid which comprises a step of preparing cDNA from RNA even in the case of its use as a template by using a DNA polymerase having reverse transcriptase activity such as BcaBEST DNA polymerase. The step of preparing cDNA from RNA may be conducted independently, and the product may be used in the process for amplifying a nucleic acid according to the invention.

In the process for synthesizing a nucleic acid and the process for amplifying a nucleic acid according to the invention, a melting temperature adjusting agent can be added to the reaction solution in order to enhance the synthetic efficiency or amplification efficiency of the nucleic acid. The melting temperature (Tm) of the nucleic acid is generally determined by the particular nucleotide sequence of a double strand forming portion in the nucleic acid. The melting temperature (Tm) can be changed by adding a melting temperature adjusting agent in the reaction solution, and thus the strength of the double strand formation in the nucleic acid can be adjusted at a fixed temperature. Many melting temperature adjusting agents frequently employed have an effect of lowering melting temperatures. The melting temperature of double strand forming portion between two nucleic acids can be lowered, and in other words, the strength of forming the double strand can be reduced by adding such melting temperature adjusting agent. Thus, the addition of such melting temperature adjusting agent into a reaction solution in the process for synthesizing a nucleic acid and the process for amplifying a nucleic acid according to the invention can efficiently change the double-stranded portion into a single strand in a nucleic acid region which is rich in GC for forming a strong double strand or in a region in which a complicated secondary structure is formed. Thus, the completion of the extension reaction with a primer makes easy the hybridization of the next primer on the aimed region, and the synthetic efficiency and amplification efficiency of a nucleic acid can be enhanced. The melting temperature adjusting agent used in the invention and its concentration in a reaction solution is appropriately selected by a person skilled in the art in consideration of the other reaction conditions which affect hybridization such as salt concentration, reaction temperature, and the like. Thus, the melting temperature adjusting agents include preferably, but not limited to, dimethyl sulfoxide (DMSO), betaine, formamide or glycerol, or any combinations thereof, and more preferably dimethyl sulfoxide (DMSO).

Furthermore, it is also possible to add an enzyme stabilizing agent to the reaction solution in the process for synthesizing nucleic acids and the process for amplifying nucleic acids according to the invention. As a result, the enzyme in the reaction mixture is stabilized, and the synthetic efficiency and amplification efficiency of nucleic acids can be enhanced. The enzyme stabilizing agents used in the present invention may be any one which is known in the art and includes glycerol without limitation thereto.

In addition, it is also possible to add a reagent for enhancing the heat resistance of enzymes such as DNA polymerase or reverse transcriptase to the reaction solution in the process for synthesizing nucleic acids and the process for amplifying nucleic acids according to the invention. As a result, the enzyme in the reaction mixture is stabilized, and the synthetic efficiency and amplification efficiency of nucleic acids can be enhanced. Such reagent may be any one which is known in the art and includes trehalose without limitation thereto.

In the process for synthesizing nucleic acids and the process for amplifying nucleic acids according to the invention, the synthesis reaction or the amplification reaction are repeated until the enzyme is inactivated or one of the reagents such as the primers has been exhausted.

In the process for synthesizing nucleic acids and the process for amplifying nucleic acids according to the invention, it is also possible to use a nucleic acid as a template nucleic acid. The term "non-natural nucleotide" herein means a nucleotide which contains bases other than the bases contained in natural nucleotides (adenine, guanine, cytosine, and thymine or uracil) and is incorporated into a nucleic acid sequence, and includes for example xanthosines, diaminopyridines, isoG, isoC (Proc Natl. Acad. Sci. USA 92, 6329-6333, 1995), and the like. Target nucleic acids containing non-natural nucleotides are generally amplified with nucleic acid amplifying enzymes having no heat resistance. On the other hand, the process for synthesizing nucleic acids and the process for amplifying nucleic acids according to the invention can be conducted isothermally for example at about 50° C., so that the nucleic acid amplifying enzymes such as DNA polymerase will not be inactivated so often as compared with the conventional PCR method. Thus, the process for synthesizing nucleic acids and the process for amplifying nucleic acids according to the invention can also be effectively employed for the amplification of non-natural nucleotide-containing target nucleic acids in which the nucleic acid-amplifying enzymes having no heat resistance are used. Enzymes used for the amplification of nucleic acids containing non-natural nucleotides may be the ones which are capable of amplifying such target nucleic acids without any further limitations, and preferably include a Y188L/E478Q mutated HIV I reverse transcriptase, an AMV reverse transcriptase, a Klenow fragment of a DNA polymerase, a 9° N DNA polymerase, a HotPub DNA polymerase, and the like (see Michael Sismour 1 et al., Biochemistry 42(28), 8598, 2003/U.S. Pat. No. 6,617,106; Michael J. Lutz et al., Bioorganic & Medical Chemistry Letters 8, 1149-1152, 1998; etc.). Moreover, it is also possible to add materials for improving the heat resistance of nucleic acid-amplifying enzymes, such as trehalose, to a reaction solution, and thus non-natural nucleotide-containing target nucleic acids can be amplified more efficiently.

It is possible to prepare quickly a single-stranded nucleic acid for immobilizing on a DNA chip, a single-stranded DNA probe for determining the base sequence or a megaprimer for the long chain PCR method by using the process for synthesizing nucleic acids or the process for amplifying nucleic acids according to the invention. For instance, it is possible to selectively amplify only a sense sequence or an antisense sequence according to objects by using the process for synthesizing nucleic acids or the process for amplifying nucleic acids according to the invention. Therefore, the process for synthesizing nucleic acids or the process for amplifying nucleic acids according to the invention are also useful as the process for producing the sense or antisense sequence of a certain target nucleic acid.

Amplified products obtained by the process for synthesizing nucleic acids or the process for amplifying nucleic acids according to the invention can be detected by any appropriate methods. One of the methods is the detection of an amplified product having a specific size by the conventional gel electrophoresis. According to this method, the amplified product can be detected with fluorescent materials such as ethidium bromide, SYBR Green, and the like. In another method, the product can also be detected by hybridizing a labeled probe having a label such as biotin with the product. Biotin can be detected by binding with fluorescent-labeled avidin or with avidin bound to an enzyme such as peroxidase.

Also, the amplified product obtained by the process for synthesizing nucleic acids or the process for amplifying nucleic acids according to the invention can be detected with an immunochromatograph. In this method, it is devised to employ a chromatographic medium with a macroscopically detectable label (immunochromatography technique). Hybridization of the amplified fragment and the labeled probe, and immobilization of a capturing probe, which is capable of hybridizing with the other different sequences in the amplified fragment, on the chromatographic medium makes it possible to trap the product at the immobilized part and to detect it in the chromatographic medium. As a consequence, macroscopically simple detection of the product can be conducted.

Further, in the process for synthesizing nucleic acids or the process for amplifying nucleic acids according to the invention, a primer immobilized on beads can be used for confirming the agglutination of the beads due to the synthesis or amplification of a nucleic acid and thus detecting the synthetic or amplification product. Also, in order to synthesize or amplify a plurality of target nucleic acids, each primer designed with regard to each of the target nucleic acids can be immobilized on beads, which are different in color, shape or the like and thus can be distinguished from one another, for the reaction of synthesizing or amplifying nucleic acids in a reaction solution involving these beads. In such case, whether the respective target nucleic acids is present or not is recognized by confirming the presence or absence of the agglutination of respective beads.

Furthermore, in the process for synthesizing nucleic acids or the process for amplifying nucleic acids according to the invention, a primer immobilized on an array such as e.g. DNA chip can be used for confirming the agglutinated nucleic acids produced on the array due to the synthesis or amplification of a nucleic acid and thus detecting the synthetic or amplification product. Also, in order to synthesize or amplify a plurality of target nucleic acids, each primer designed with regard to each of the target nucleic acids can be immobilized on an array, which can be distinguished from one another, for the reaction of synthesizing or amplifying nucleic acids in a reaction solution involving the array. In such case, whether the respective target nucleic acids is present or not is recognized by confirming the presence or absence of the agglutinated nucleic acid at the corresponding positions on the array.

It is also possible to use an intercalater in place of the confirmation of the agglutinated nucleic acid.

The amplified fragment obtained by the process for amplifying a nucleic acid according to the invention is composed of ordinary bases, and thus can be subcloned into an appropriate vector by using a restriction enzyme site within the amplified fragment. In addition, it is also possible to carry out treatment with restriction enzymes such as RFLP, which can-be employed widely in the field of genetic test as well. Also, since the amplified fragment obtained by the process for amplifying a nucleic acid according to the invention is composed of ordinary bases, the incorporation of the promoter sequence of an RNA polymerase into the amplified fragment makes it possible to synthesize an RNA directly from the amplified fragment, and the RNA can also be used as an RNA probe.

Furthermore, in the process for synthesizing nucleic acids or the process for amplifying nucleic acids according to the invention, a base labeled with biotin or a fluorescent material can be used in place of an ordinary dNTP to prepare a DNA probe labeled with biotin or the fluorescent material.

The single-stranded nucleic acid prepared by the process for synthesizing nucleic acids or the process for amplifying nucleic acids according to the invention can be used as a DNA fragment immobilized on the DNA chip. That is to say, the process for synthesizing nucleic acids or the process for amplifying nucleic acids according to the invention can be applied also to the method for preparing a DNA strand immobilized in the preparation of a DNA chip. It is also possible to prepare a DNA chip by preliminarily immobilizing the 5'-end of a primer on the DNA chip, on which the synthesis or amplification of a nucleic acid is carried out. It is also possible to conduct the real time detection together with the synthesis or amplification of a nucleic acid on the DNA chip by preliminarily adding a fluorescent labeling probe prior to the synthesis or amplification of a nucleic acid.

In order to practice the process for synthesizing nucleic acids or the process for amplifying nucleic acids according to the invention, reagents involved in the process can be combined to make a kit. Thus, the kit according to the invention comprises a primer or a primer set according to the invention. Also, the process for synthesizing nucleic acids or the process for amplifying nucleic acids according to the invention has an advantage that the process requires no primers other than the primer or the primer set according to the invention. Thus, according to the preferred embodiments of the invention, the kit according to the invention comprises no primer ingredients other than the primer or the primer set according to the invention. The kit according to the invention may further include reagents, reaction vessels, instructions described above, and the like.

EXAMPLES

The invention is further described more particularly in the following examples, which should not be construed in any way as restrictions on the invention.

Example 1

In this example, the amplification of a human STS DYS237 gene was attempted with Human DNA (Clontech) as a template. Primers employed were as follows. These primers were synthesized by the consignment to ESPEC OLIGO SERVICE CORP.

Figure 2:
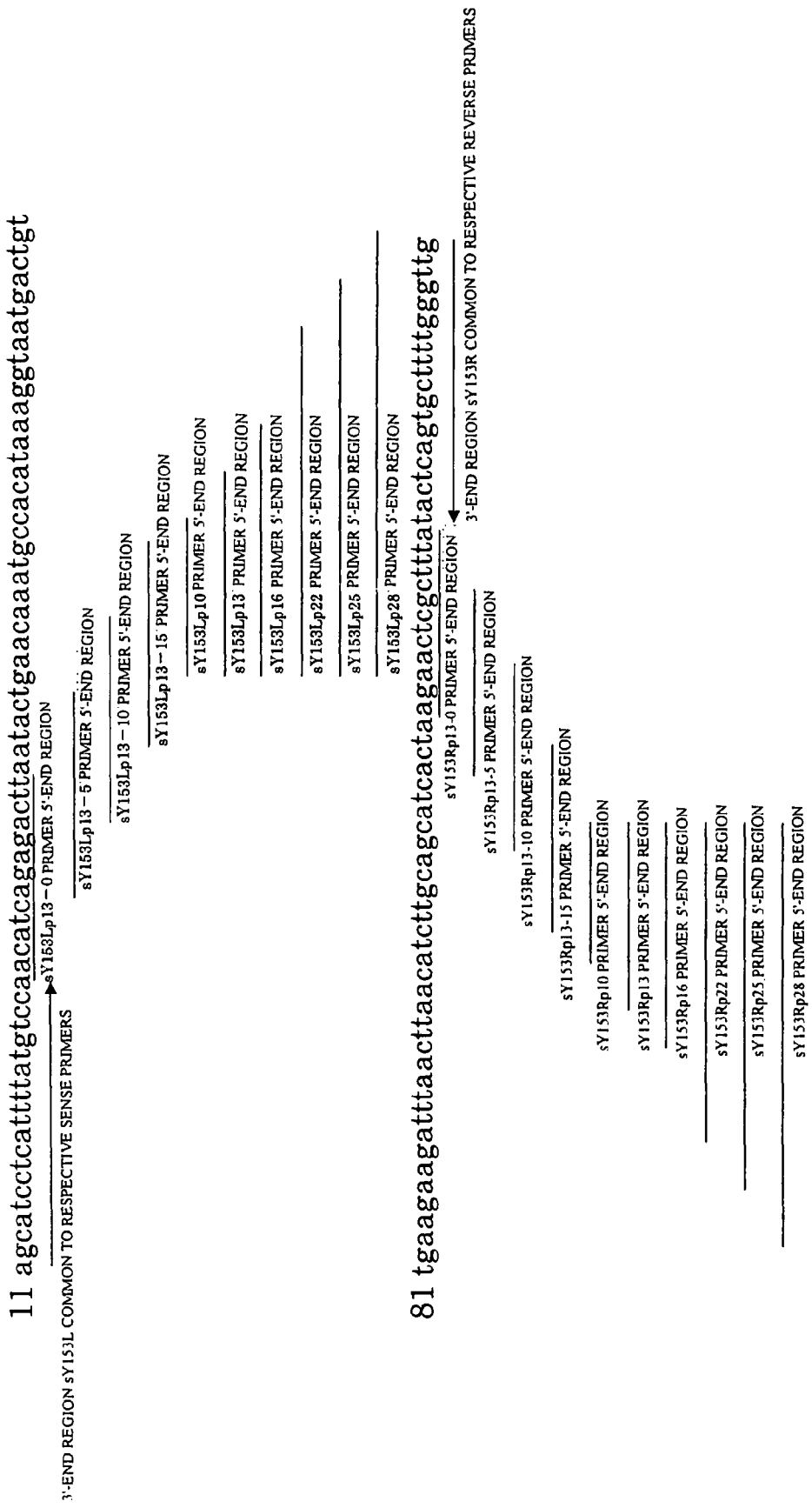
FIG. 2 shows the positions of sequences of a primer used for the amplification of a human STS DYS237 gene in the 5'-side and the 3'-side (SEQ ID NO: 41).

The features of the primers used in the experiment were described below. The relationships of respective primers to the template were as illustrated in FIG. 2. In this connection, underlined parts in the following sequences represent 3'-end regions common to each of sense primers and antisense primers, respectively.

Primer set 1: a combination of primers comprising solely sequences annealing to the template (20 mer);

```
SY153L:  GCATCCTCATTTTATGTCCA;  (SEQ ID NO: 1)
SY153R:  CAACCCAAAAGCACTGAGTA.  (SEQ ID NO: 2)
```

Primer set 2: a combination of primers in which after annealing of sequences placed in the 3'-end side of the respective primers (20 mer: sequences identical to those in Primer set 1) to the template and extension reaction, a sequence in the 5'-end side (13 mer) is hybridized with a region starting from a base downstream of the 3'-end portion of the respective primers on a strand extended from the primer;

```
                                        (SEQ ID NO: 3)
SY153LP13-0:  AAGTCTCTGATGTGCATCCTCATTTTATGTCCA;

(SEQ ID NO: 4)
SY153RP13-0:  AGAACTCGCTTTACAACCCAAAAGCACTGAGTA.
```

Primer set 3: a combination of primers in which after annealing of sequences placed in the 3'-end side of the respective primers (20 mer: sequences identical to those in Primer set 1) to the template and extension reaction, a sequence in the 5'-end side (13 mer) is hybridized with a region starting from six bases downstream of the 3'-end portion of the respective primers on a strand extended from the primer;

```
                                        (SEQ ID NO: 5)
SY153LP13-5:  GTATTAAGTCTCTGCATCCTCATTTTATGTCCA;

(SEQ ID NO: 6)
SY1535P13-5:  CACTAAGAACTCGCAACCCAAAAGCACTGAGTA.
```

Primer set 4: a combination of primers in which after annealing of sequences placed in the 3'-end side of the respective primers (20 mer: sequences identical to those in Primer set 1) to the template and extension reaction, a sequence in the 5'-end side (13 mer) is hybridized with a region starting from 11 bases downstream of the 3'-end portion of the respective primers on a strand extended from the primer;

```
                                        (SEQ ID NO: 7)
SY153LP13-10:  GTTCAGTATTAAGGCATCCTCATTTTATGTCCA;

(SEQ ID NO: 8)
SY153RP13-10:  AGCATCACTAAGACAACCCAAAAGCACTGAGTA.
```

Primer set 5: a combination of primers in which after annealing of sequences placed in the 3'-end side of the respective primers (20 mer: sequences identical to those in Primer set 1) to the template and extension reaction, a sequence in the 5'-end side (13 mer) is hybridized with a region starting from 16 bases downstream of the 3'-end portion of the respective primers on a strand extended from the primer;

```
                                        (SEQ ID NO: 9)
SY153LP13-15:  CATTTGTTCAGTAGCATCCTCATTTTATGTCCA;

(SEQ ID NO: 10)
SY153RP13-15:  CTTGCAGCATCACCAACCCAAAAGCACTGAGTA.
```

Primer set 6: a combination of primers in which after annealing of sequences placed in the 3'-end side of the respective primers (20 mer: sequences identical to those in Primer set 1) to the template and extension reaction, a sequence in the 5'-end side (10 mer) is hybridized with a region starting from 21 bases downstream of the 3'-end portion of the respective primers on a strand extended from the primer;

```
                                        (SEQ ID NO: 11)
SY153LP10:  GGCATTTGTTGCATCCTCATTTTATGTCCA;

(SEQ ID NO: 12)
SY153RP10:  ATCTTGCAGCCAACCCAAAAGCACTGAGTA.
```

Primer set 7: a combination of primers in which after annealing of sequences placed in the 3'-end side of the respective primers (20 mer: sequences identical to those in Primer set 1) to the template and extension reaction, a sequence in the 5'-end side (13 mer) is hybridized with a region starting from 21 bases downstream of the 3'-end portion of the respective primers on a strand extended from the primer;

```
                                        (SEQ ID NO: 13)
SY153LP13:  TGTGGCATTTGTTGCATCCTCATTTTATGTCCA;

(SEQ ID NO: 14)
SY153RP13:  AACATCTTGCAGCCAACCCAAAAGCACTGAGTA.
```

Primer set 8: a combination of primers in which after annealing of sequences placed in the 3'-end side of the respective primers (20 mer: sequences identical to those in Primer set 1) to the template and extension reaction, a sequence in the 5'-end side (16 mer) is hybridized with a region starting from 21 bases downstream of the 3'-end portion of the respective primers on a strand extended from the primer;

```
                                        (SEQ ID NO: 15)
SY153LP16:  TTATGTGGCATTTGTTGCATCCTCATTTTATGTCCA;

(SEQ ID NO: 16)
SY153RP16:  CTTAACATCTTGCAGCCAACCCAAAAGCACTGAGTA.
```

Primer set 9: a combination of primers in which after annealing of sequences placed in the 3'-end side of the respective primers (20 mer: sequences identical to those in Primer set 1) to the template and extension reaction, a sequence in the 5'-end side (22 mer) is hybridized with a region starting from 21 bases downstream of the 3'-end portion of the respective primers on a strand extended from the primer;

```
SY153LP22:
                                        (SEQ ID NO: 17)
TTACCTTTATGTGGCATTTGTTGCATCCTCATTTTATGTCCA;

SY153RP22:
                                        (SEQ ID NO: 18)
ATTTAACTTAACATCTTGCAGCCAACCCAAAAGCACTGAGTA.
```

Primer set 10: a combination of primers in which after annealing of sequences placed in the 3'-end side of the respective primers (20 mer: sequences identical to those in Primer set 1) to the template and extension reaction, a sequence in the 5'-end side (25 mer) is hybridized with a region starting from 21. bases downstream of the 3'-end portion of the respective primers on a strand extended from the primer;

SY153LP25:

(SEQ ID NO: 19)
TCATTACCTTTATGTGGCATTTGTT<u>GCATCCTCATTTTATGTCCA</u>;

SY153RP25:

(SEQ ID NO: 20)
AAGATTTAACTTAACATCTTGCAGC<u>CAACCCAAAAGCACTGAGTA</u>.

Primer set 11: a combination of primers in which after annealing of sequences placed in the 3'-end side of the respective primers (20 mer: sequences identical to those in Primer set 1) to the template and extension reaction, a sequence in the 5'-end side (28 mer) is hybridized with a region starting from 21 bases downstream of the 3'-end portion of the respective primers on a strand extended from the primer;

SY153LP28:

(SEQ ID NO: 21)
CAGTCATTACCTTTATGTGGCATTTGTT<u>GCATCCTCATTTTATGTCCA</u>;

SY153RP28:

(SEQ ID NO: 22)
AAGAAGATTTAACTTAACATCTTGCAGC<u>CAACCCAAAAGCACTGAGTA</u>.

A reaction mixture (25 µl) of Tris-HCl (20 mM, pH8.8), KCl (10 mM), (NH$_4$)$_2$SO$_4$ (10 mM), MgSO$_4$ (2 mM), Triton X-100 (0.1%), dNTP (0.4 mM), a primer pair (100 pmol, resp.), a template DNA (100 ng), and Bst DNA polymerase (8U; NEW ENGLAND BioLabs) was prepared, and incubated at 60° C. for 20, 40, or 60 minutes.

Figure 5:
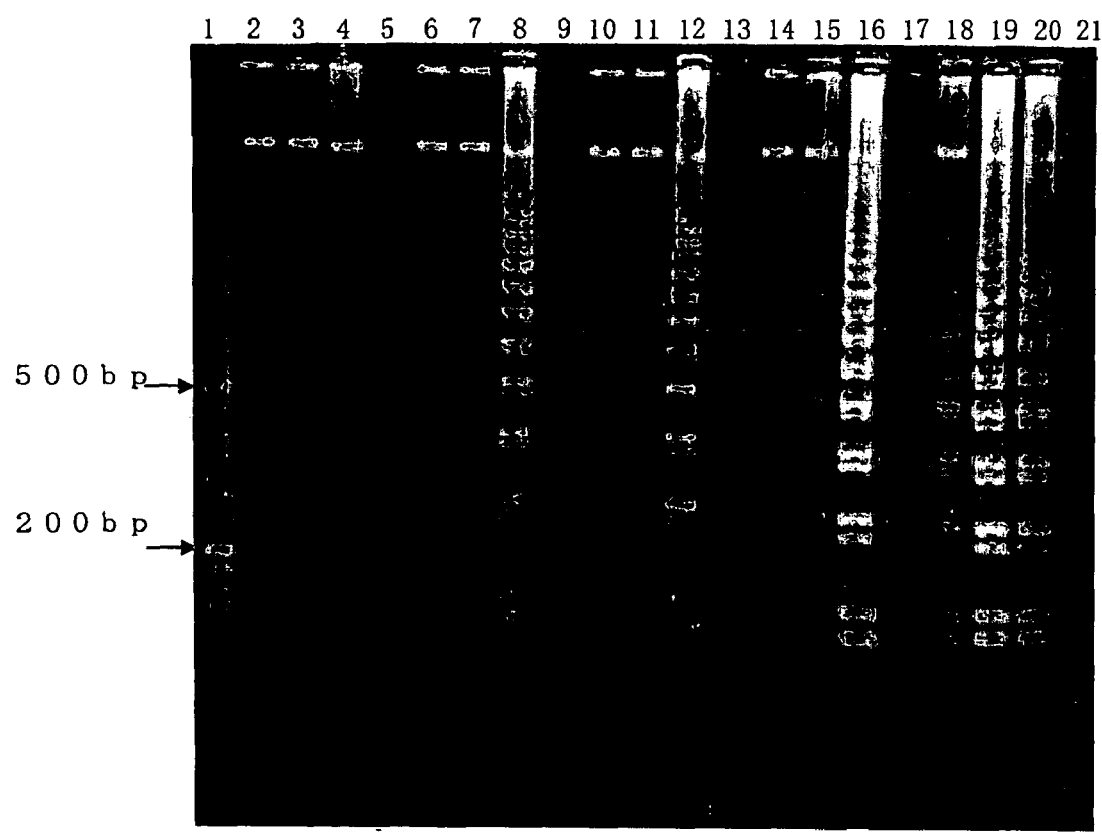
FIG. 5 shows the amplification of a human STS DYS237 gene under a variety of conditions.
Figure 6:
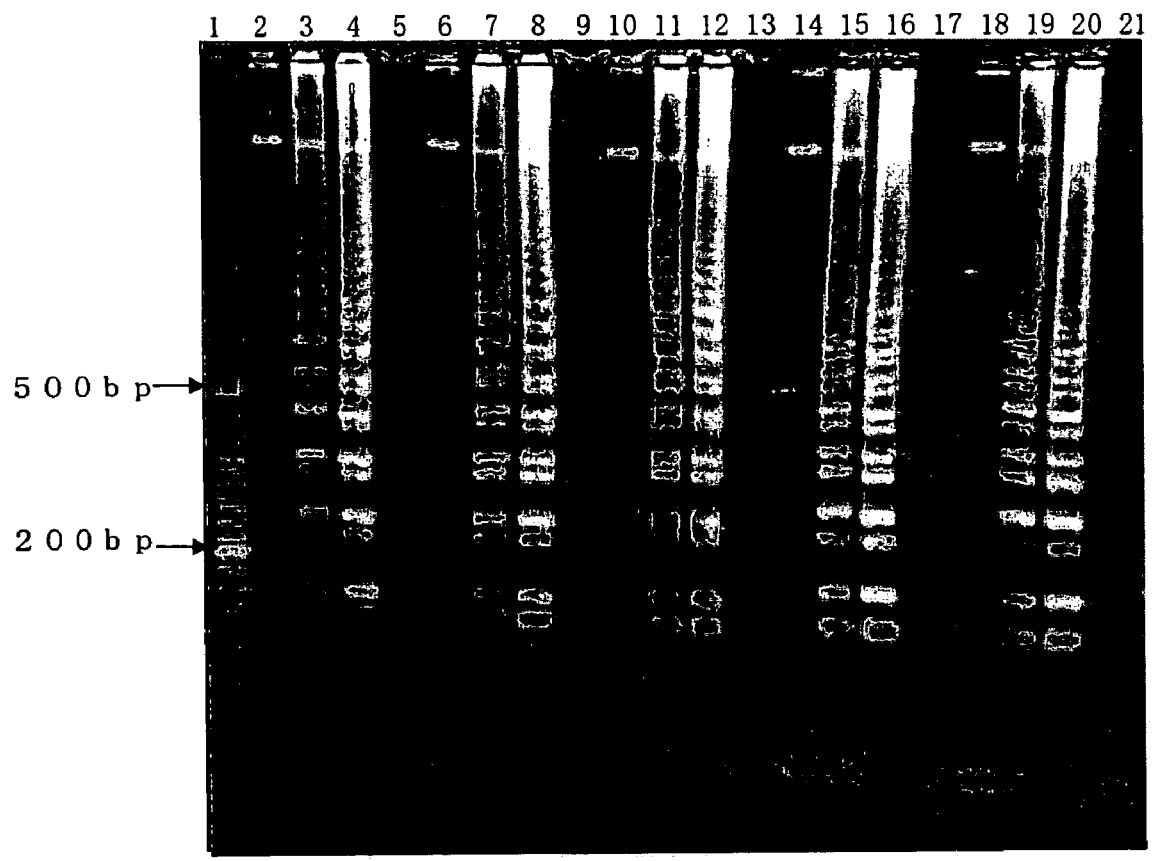
FIG. 6 shows the amplification of a human STS DYS237 gene under a variety of conditions.
Figure 7:
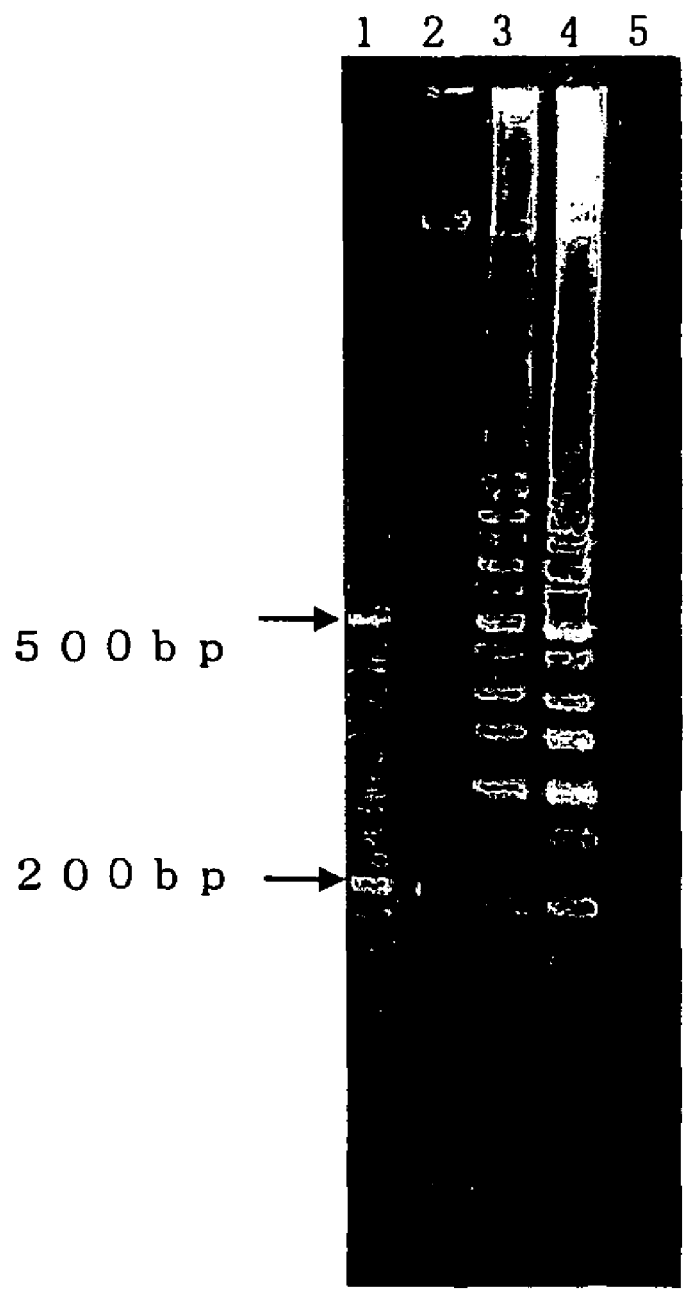
FIG. 7 shows the amplification of a human STS DYS237 gene under a variety of conditions.

A 5 µl portion of each mixture was subjected to electrophoresis in 3% NuSieve GTG Agarose (manufactured by BioWhittaker Molecular Applications (BMA); purchased from Takara Bio Inc.; "NuSieve" is the registered trademark of BMA). Results are shown in FIGS. 5, 6 and 7. Samples in respective lanes in these figures are shown in the following Tables 1-3.

TABLE 1

Explanation of lanes of electrophoretic photograms in FIG. 5

| Lane | Primer | Template | Reaction Time (min.) |
|---|---|---|---|
| 1 | DNA size marker (20 bp ladder) | | |
| 2 | Primer set 1 | Yes | 20 |
| 3 | Primer set 1 | Yes | 40 |
| 4 | Primer set 1 | Yes | 60 |
| 5 | Primer set 1 | No | 60 |
| 6 | Primer set 2 | Yes | 20 |
| 7 | Primer set 2 | Yes | 40 |
| 8 | Primer set 2 | Yes | 60 |
| 9 | Primer set 2 | No | 60 |
| 10 | Primer set 3 | Yes | 20 |
| 11 | Primer set 3 | Yes | 40 |
| 12 | Primer set 3 | Yes | 60 |
| 13 | Primer set 3 | No | 60 |
| 14 | Primer set 4 | Yes | 20 |
| 15 | Primer set 4 | Yes | 40 |
| 16 | Primer set 4 | Yes | 60 |
| 17 | Primer set 4 | No | 60 |
| 18 | Primer set 5 | Yes | 20 |
| 19 | Primer set 5 | Yes | 40 |
| 20 | Primer set 5 | Yes | 60 |
| 21 | Primer set 5 | No | 60 |

TABLE 2

Explanation of lanes of electrophoretic photograms in FIG. 6

| Lane | Primer | Template | Reaction Time (min.) |
|---|---|---|---|
| 1 | DNA size marker (20 bp ladder) | | |
| 2 | Primer set 6 | Yes | 20 |
| 3 | Primer set 6 | Yes | 40 |
| 4 | Primer set 6 | Yes | 60 |
| 5 | Primer set 6 | No | 60 |
| 6 | Primer set 7 | Yes | 20 |
| 7 | Primer set 7 | Yes | 40 |
| 8 | Primer set 7 | Yes | 60 |
| 9 | Primer set 7 | No | 60 |
| 10 | Primer set 8 | Yes | 20 |
| 11 | Primer set 8 | Yes | 40 |
| 12 | Primer set 8 | Yes | 60 |
| 13 | Primer set 8 | No | 60 |
| 14 | Primer set 9 | Yes | 20 |
| 15 | Primer set 9 | Yes | 40 |
| 16 | Primer set 9 | Yes | 60 |
| 17 | Primer set 9 | No | 60 |
| 18 | Primer set 10 | Yes | 20 |
| 19 | Primer set 10 | Yes | 40 |
| 20 | Primer set 10 | Yes | 60 |
| 21 | Primer set 10 | No | 60 |

TABLE 3

Explanation of lanes of electrophoretic photograms in FIG. 7

| Lane | Primer | Template | Reaction Time (min.) |
|---|---|---|---|
| 1 | DNA size marker (20 bp ladder) | | |
| 2 | Primer set 11 | Yes | 20 |
| 3 | Primer set 11 | Yes | 40 |
| 4 | Primer set 11 | Yes | 60 |
| 5 | Primer set 11 | No | 60 |

In Lanes 5, 9, 13, 17 and 21 of respective Figures, no bands other than those of stained unreacted primers were observed due to the addition of no template.

In Lanes 2 and 3 of FIG. 5, bands of an unreacted primer and a template having a high molecular size were confirmed because of the addition of a template. However, no amplified products were confirmed because of insufficient reaction time. As shown in Lane 4 of FIG. 5, in the sample having a template added thereto and reacted for 60 minutes were obtained an amplified product, which was in the form of a ladder in the low size region and of a smear in the high size region. In Lanes 2-5 of FIG. 5, Primer set 1 containing solely an oligonucleotide (20 mer) which anneals to a template was used and no synthetic reaction occurred, so that no amplified products as the object were obtained.

In Lane 6 and the subsequent lanes of FIG. 5, there is shown the results of amplifications with a primer set in which after annealing of sequences placed in the 3'-end side of the respective primers (20 mer: sequences identical to those in Primer set 1) to the template, a sequence in the 5'-end side is hybridized with a region starting from bases downstream of the 3'-end portion of the respective primers on the extended strand of the primers.

As shown in Lanes 8 and 12 of FIG. 5, when Primer sets 2 or 3 were used, it was possible to obtain the aimed amplification product in a reaction time of 60 minutes. Of the low size bands, the band in the vicinity of ca. 160 bp is an expected product of the synthetic reaction of the invention.

Further, as shown in Lanes 15 and 16 of FIG. 5, Lanes 3, 4, 7, 8, 11, 12, 15, 16, 19 and 20 of FIG. 6, and Lanes 3 and 4 of FIG. 7, it was possible to obtain the aimed amplification product in a reaction time of 40 minutes or more when Primer sets 4, 6, 7, 8, 9, 10 and 11 were used. Of the low size bands, the band in the vicinity of ca. 160 bp is an expected product of the synthetic reaction of the invention.

In addition, as shown in Lanes 18-20 of FIG. 5, it was possible to obtain the aimed amplification product in a reaction time of 20 minutes or more when Primer set 5-was used. Of the low size bands, the band in the vicinity of ca. 160 bp is an expected product of the synthetic reaction of the invention.

When the distance between the region corresponding to the sequence in the 3'-end side of the primer on the extended strand of the primer and the region with which the sequence in the 5'-end side hybridizes is comparatively small as in Primer sets 2 and 3, it is considered that a long reaction time is required because most of the sequence on a template having the same sequence to which the next primer is to be annealed remains as a double strand and the subsequent annealing hardly occurs.

Also, when the distance between the region corresponding to the sequence in the 3'-end side of the primer on the extended strand of the primer and the region with which the sequence in the 5'-end side hybridizes is comparatively large as in Primer sets 6-11, it is considered that a comparatively long reaction time is required because the folding efficiency of the sequence in the 5'-end side of each primer is lowered.

On the other hand, when the distance between the region corresponding to the sequence in the 3'-end side of the primer on the extended strand of the primer and the region with which the sequence in the 5'-end side hybridizes is not excessively small or excessively large as in Primer set 5, it is considered that the most efficient amplification can be performed in the invention.

Example 2

In this example, the amplification of an sY160 gene was attempted with Human DNA (Clontech) as a template. Primers employed were as follows. These primers were synthesized by the consignment to ESPEC OLIGO SERVICE CORP.

The features of the primers used in the experiment were described below. The relationships of respective primers to the template were as illustrated in FIG. 3. In this connection, underlined parts in the following sequences represent 3'-end regions common to each of sense primers and antisense primers, respectively.

Primer set 12: a combination of a sense primer in which after annealing of a sequenceplaced in the 3'-end side of a primer (20 mer) to the template and extension reaction, a sequence in the 5'-end side (13 mer) is hybridized with a region starting from 27 bases downstream of the 3'-end portion of the primer on a strand extended from the primer, and an antisense primer in which after annealing of a sequence placed in the 3'-end side of a primer (20 mer) to the template and extension reaction, a sequence in the 5'-end side (13 mer) is hybridized with a region starting from 21 bases downstream of the 3'-end portion of the primer on a strand extended from the primer;

(SEQ ID NO: 23)
SY160LP13: ATTCGATTCCGTT<u>TACGGGTCTCGAATGGAATA</u>;

(SEQ ID NO: 24)
SY160RP13: CTAAATCGAATGG<u>TCATTGCATTCCTTTCCATT</u>.

Primer set 13: a combination of a sense primer in which after annealing of a sequence placed in the 3'-end side of a primer (20 mer: sequence identical to that in Primer set 12) to the template and extension reaction, a sequence in the 5'-end side (13 mer) is hybridized with a region starting from 27 bases downstream of the 3'-end portion of the primer on a strand extended from the primer, and an antisense primer in which after annealing of a sequence placed in the 3'-end side of a primer (20 mer: sequence identical to that in Primer set 12) to the template and extension reaction, a sequence in the 5'-end side (16 mer) is hybridized with a region starting from 21 bases downstream of the 3'-end portion of the primer on a strand extended from the primer;

(SEQ ID NO: 25)
SY160LP16: GACATTCGATTCCGTT<u>TACGGGTCTGGAATGGAATA</u>;

(SEQ ID NO: 26)
SY160RP16: GAACTAAATCGAATGG<u>TCATTGCATTCCTTTCCATT</u>.

A reaction mixture (25 µl) of Tris-HCl (20 mM, pH8.8), KCl (10 mM), $(NH_4)_2SO_4$ (10 mM), $MgSO_4$ (2 mM), Triton X-100 (0.1%), dNTP (0.4 mM), a primer pair (100 pmol, resp.), a template DNA (100 ng), and Bst DNA polymerase (8U; NEW ENGLAND BioLabs) was prepared, and incubated at 60° C. for 60 or 90 minutes.

Figure 8:
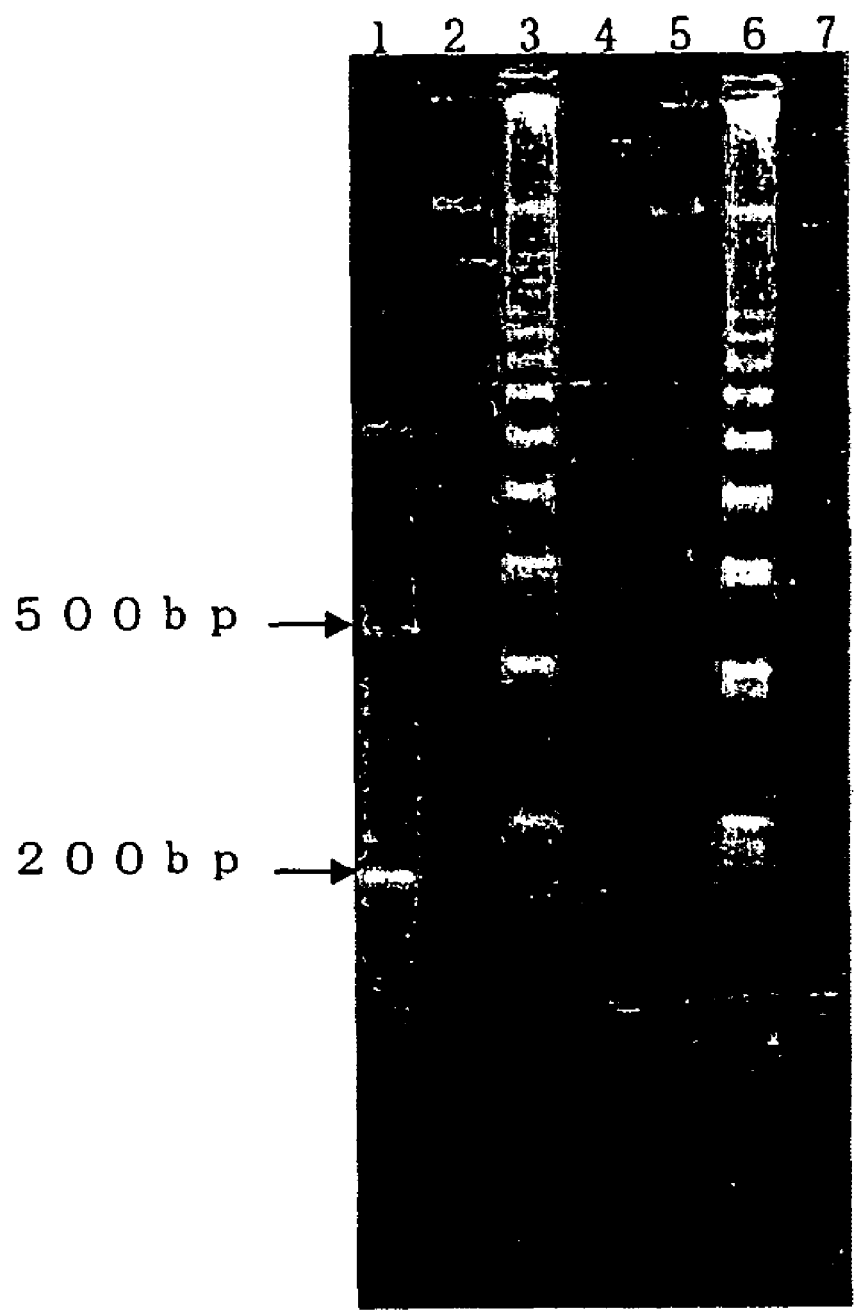
FIG. 8 shows the amplification of an sY160 gene under a variety of conditions.

A 5 µl portion of each mixture was subjected to electrophoresis in 3% NuSieve GTG Agarose (manufactured by BioWhittaker Molecular Applications (BMA); purchased from Takara Bio Inc.; "NuSieve" is the registered trademark of BMA). Results are shown in FIG. 8. Samples in respective lanes in these figures are shown in the following Table 4.

TABLE 4

Explanation of lanes of electrophoretic photograms in FIG. 8

| Lane | Primer | Template | Reaction Time (min.) |
|---|---|---|---|
| 1 | DNA size marker (20 bp ladder) | | |
| 2 | Primer set 12 | Yes | 60 |
| 3 | Primer set 12 | Yes | 90 |
| 4 | Primer set 12 | No | 90 |
| 5 | Primer set 13 | Yes | 60 |
| 6 | Primer set 13 | Yes | 90 |
| 7 | Primer set 13 | No | 90 |

In Lanes 4 and 7, no bands other than those of stained unreacted primers were observed due to the addition of no template.

In Lanes 2 and 5, bands of an unreacted primer and a template having a high molecular size were confirmed because of the addition of a template. However, no amplified products were confirmed because of insufficient reaction time. As shown in Lane 3 and 6, in the sample having a template added thereto and reacted for 90 minutes were obtained an aimed amplified product in a satisfactory amount. Of the low size bands, the one in the vicinity of ca. 260 bp is an expected product of the synthetic reaction of the invention.

Example 3

In this example, the amplification of an M13mp18RF DNA (phage vector; TAKARA BIO INC.) was attempted with the same DNA as a template. Primers employed were as follows. These primers were synthesized by the consignment to ESPEC OLIGO SERVICE CORP.

Figure 4:
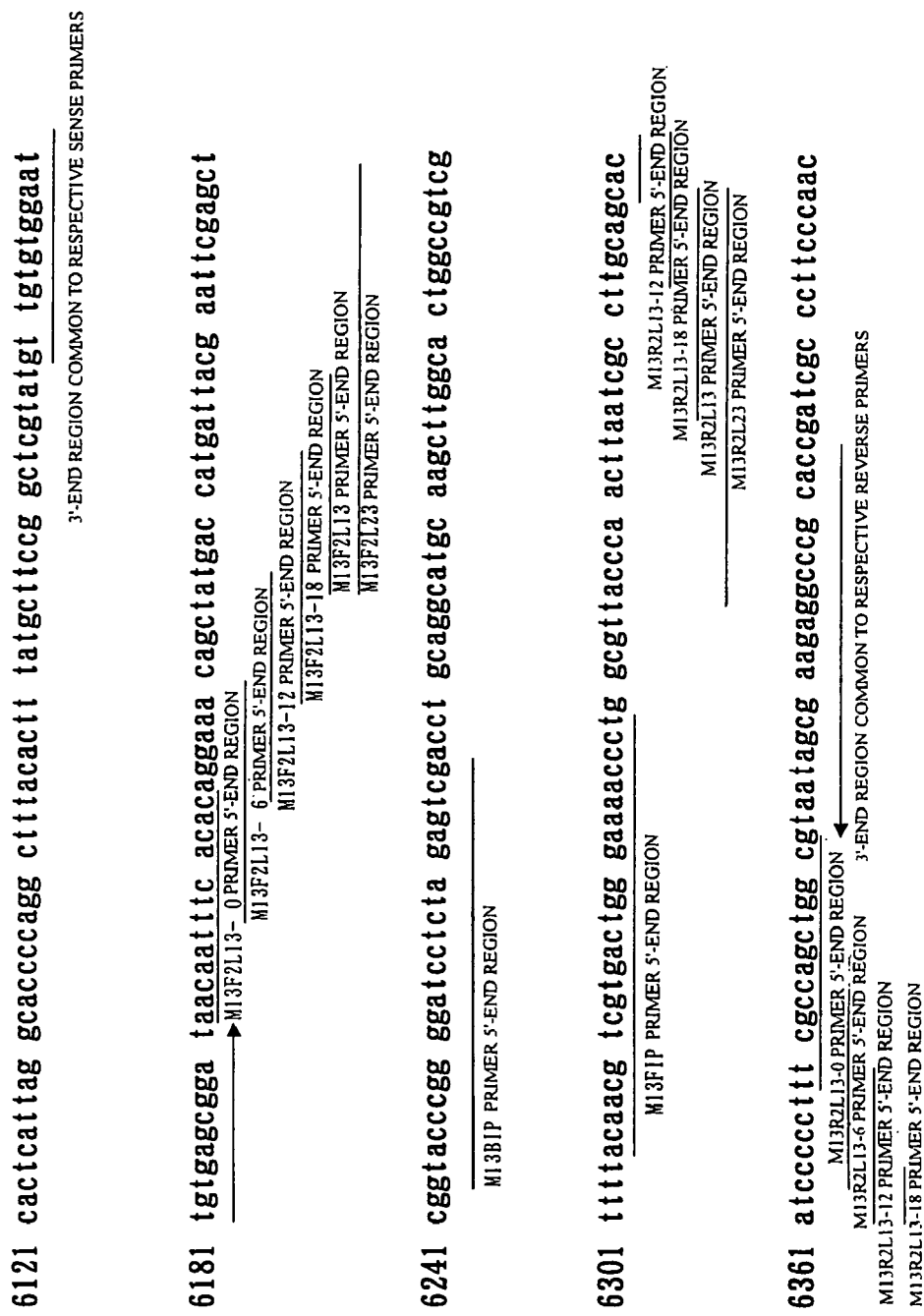
FIG. 4 shows the positions of a primer used for the amplification of an M13mp18RT DNA in the 5'-side and 3'-side (SEQ ID NO: 43).

The features of the primers used in the experiment were described below. The relationships of respective primers to the template were as illustrated in FIG. 4. In this connection, underlined parts in the following sequences represent 3'-end regions common to each of sense primers and antisense primers, respectively.

Primer set 14: a combination of a sense primer in which after annealing of a sequence placed in the 3'-end side of a primer (24 mer) to the template and extension reaction, a sequence in the 5'-end side (24 mer) is hybridized with a region starting from 51 bases downstream of the 3'-end portion of the primer on a strand extended from the primer, and an antisense primer in which after annealing of a sequence placed in the 3'-end side of a primer (22 mer) to the template and extension reaction, a sequence in the 5'-end side (25 mer) is hybridized with a region starting from 54 bases downstream of the 3'-end portion of the primer on a strand extended from the primer;

M13BIP:
(SEQ ID NO: 27)
CGACTCTAGAGGATCCCCGGGTAC<u>TGTTGTGTGGAATTGTGAGCGGAT</u>;

M13FIP:
(SEQ ID NO: 28)
ACAACGTCGTGACTGGGAAAACCC<u>TGTGCGGGCCTCTTCGCTATTAC</u>.

Primer set 15: a combination of a sense primer in which after annealing of a sequence placed in the 3'-end side of a primer (24 mer: sequence identical to that in Primer set 14) to the template and extension reaction, a sequence in the 5'-end side (13 mer) is hybridized with a region starting from one base downstream of the 3'-end portion of the primer on a strand extended from the primer, and an antisense primer in which after annealing of a sequence placed in the 3'-end side of a primer (22 mer: sequence identical to that in Primer set 14) to the template and extension reaction, a sequence in the 5'-end side (13 mer) is hybridized with a region starting from one base downstream of the 3'-end portion of the primer on a strand extended from the primer;

(SEQ ID NO: 29)
M13F2L13-0: GTGTGAAATTGTT<u>TGTTGTGTGGAATTGTGAGCGGAT</u>;

(SEQ ID NO: 30)
M13R2L13-0: TTCGCCAGCTGGC<u>GTGCGGGCCTCTTCGCTATTAC</u>.

Primer set 16: a combination of a sense primer in which after annealing of a sequence placed in the 3'-end side of a primer (24 mer: sequence identical to that in Primer set 14) to the template and extension reaction, a sequence in the 5'-end side (13 mer) is hybridized with a region starting from seven bases downstream of the 3'-end portion of the primer on a strand extended from the primer, and an antisense primer in which after annealing of a sequence placed in the 3'-end side of a primer (22 mer: sequence identical to that in Primer set 14) to the template and extension reaction, a sequence in the 5'-end side (13 mer) is hybridized with a region starting from seven bases downstream of the 3'-end portion of the primer on a strand extended from the primer;

(SEQ ID NO: 31)
M13F2L13-6: TTTCCTGTGTGAA<u>TGTTGTGTGGAATTGTGAGCGGAT</u>;

(SEQ ID NO: 32)
M13R2L13-6: CCCCCTTTCGCCA<u>GTGCGGGCCTCTTCGCTATTAC</u>.

Primer set 17: a combination of a sense primer in which after annealing of a sequence placed in the 3'-end side of a primer (24 mer: sequence identical to that in Primer set 14) to the template and extension reaction, a sequence in the 5'-end side (13 mer) is hybridized with a region starting from 13 bases downstream of the 3'-end portion of the primer on a strand extended from the primer, and an antisense primer in which after annealing of a sequence placed in the 3'-end side of a primer (22 mer: sequence identical to that in Primer set 14) to the template and extension reaction, a sequence in the 5'-end side (13 mer) is hybridized with a region starting from 13 bases downstream of the 3'-end portion of the primer on a strand extended from the primer;

M13F2L13-12:
(SEQ ID NO: 33)
TAGCTGTTTCCTG<u>TGTTGTGTGGAATTGTGAGCGGAT</u>;

M13R2L13-12:
(SEQ ID NO: 34)
AGCACATCCCCCT<u>GTGCGGGCCTCTTCGCTATTAC</u>.

Primer set 18: a combination of a sense primer in which after annealing of a sequence placed in the 3'-end side of a primer (24 mer: sequence identical to that in Primer set 14) to the template and extension reaction, a sequence in the 5'-end side (13 mer) is hybridized with a region starting from 19 bases downstream of the 3'-end portion of the primer on a strand extended from the primer, and an antisense primer in which after annealing of a sequence placed in the 3'-end side of a primer (22 mer: sequence identical to that in Primer set 14) to the template and extension reaction, a sequence in the 5'-end side (13 mer) is hybridized with a region starting from 19 bases downstream of the 3'-end portion of the primer on a strand extended from the primer;

M13F2L13-18:
(SEQ ID NO: 35)
TGGTCATAGCTGT<u>TGTTGTGTGGAATTGTGAGCGGAT</u>;

M13R2L13-18:
(SEQ ID NO: 36)
CCTTGCAGCACAT<u>GTGCGGGCCTCTTCGCTATTAC</u>.

Primer set 19: a combination of a sense primer in which after annealing of a sequence placed in the 3'-end side of a primer (24 mer: sequence identical to that in Primer set 14) to the template and extension reaction, a sequence in the 5'-end side (13 mer) is hybridized with a region starting from 25 bases downstream of the 3'-end portion of the primer on a strand extended from the primer, and an antisense primer in which after annealing of a sequence placed in the 3'-end side of a primer (22 mer: sequence identical to that in Primer set 14) to the template and extension reaction, a sequence in the 5'-end side (13 mer) is hybridized with a region starting from 23 bases downstream of the 3'-end portion of the primer on a strand extended from the primer;

(SEQ ID NO: 37)
M13F2L13: TAATCATGGTCAT<u>TGTTGTGTGGAATTGTGAGCGGAT</u>;

(SEQ ID NO: 38)
M13R3L13: TCGCCTTGCAGCA<u>GTGCGGGCCTCTTCGCTATTAC</u>.

Primer set 20: a combination of a sense primer in which after annealing of a sequence placed in the 3'-end side of a primer (24 mer: sequence identical to that in Primer set 14) to the template and extension reaction, a sequence in the 5'-end side (23 mer) is hybridized with a region starting from 25 bases downstream of the 3'-end portion of the primer on a strand extended from the primer, and an antisense primer in which after annealing of a sequence placed in the 3'-end side of a primer (22 mer: sequence identical to that in Primer set 14) to the template and extension reaction, a sequence in the 5'-end side (23 mer) is hybridized with a region starting from 23 bases downstream of the 3'-end portion of the primer on a strand extended from the primer;

M13F2L23:
(SEQ ID NO: 39)
CTCGAATTCGTAATCATGGTCATTGTTGTGTGGAATTGTGAGCGGAT;

M13R3L23:
(SEQ ID NO: 40)
CCCAACTTAATCGCCTTGCAGCAGTGCGGGCCTCTTCGCTATTAC.

A reaction mixture (25 µl) of Tris-HCl (20 mM, pH8.8), KCl (10 mM), $(NH_4)_2SO_4$ (10 mM), $MgSO_4$ (2 mM), Triton X-100 (0.1%), dNTP (0.4 mM), a primer pair (100 pmol, resp.), a template DNA (0.05 µg), and Bst DNA polymerase (8U; NEW ENGLAND BioLabs) was prepared, and incubated at 65° C. for 20-120 minutes.

Figure 9:
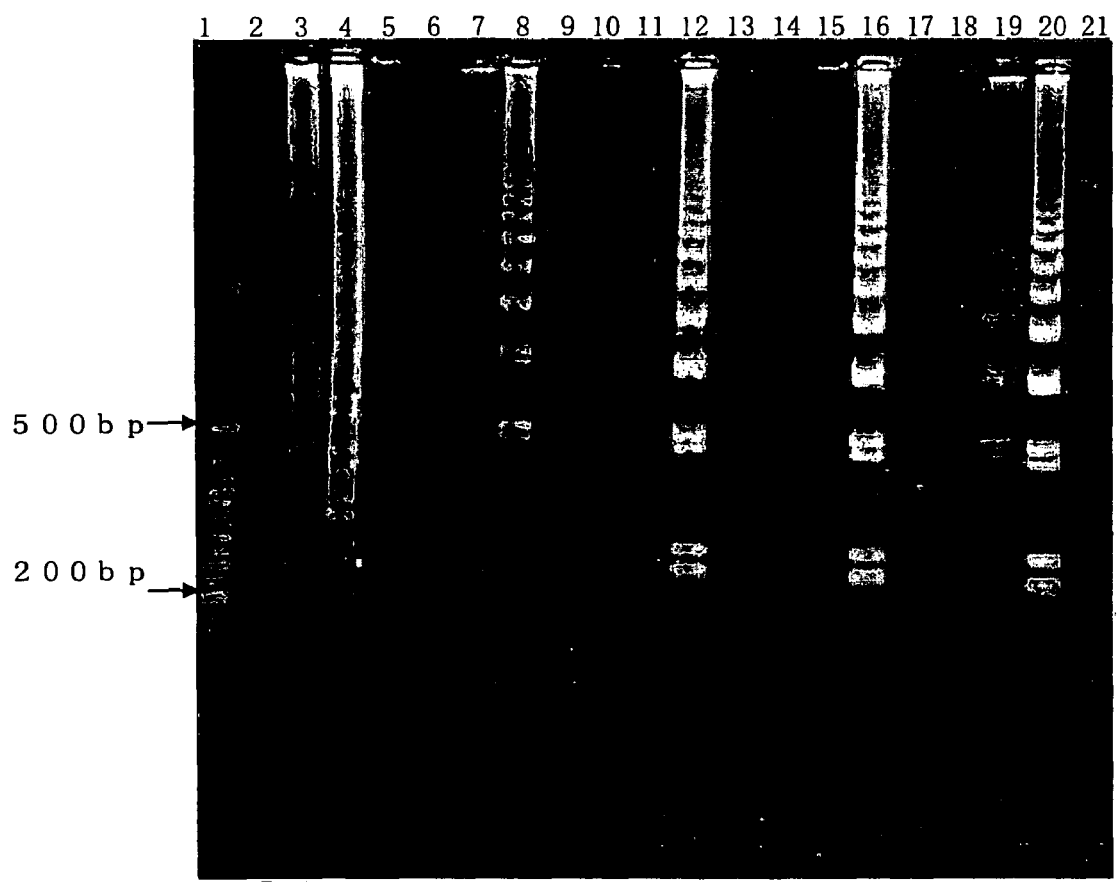
FIG. 9 shows the amplification of an M13mp18RT DNA gene under a variety of conditions.
Figure 10:
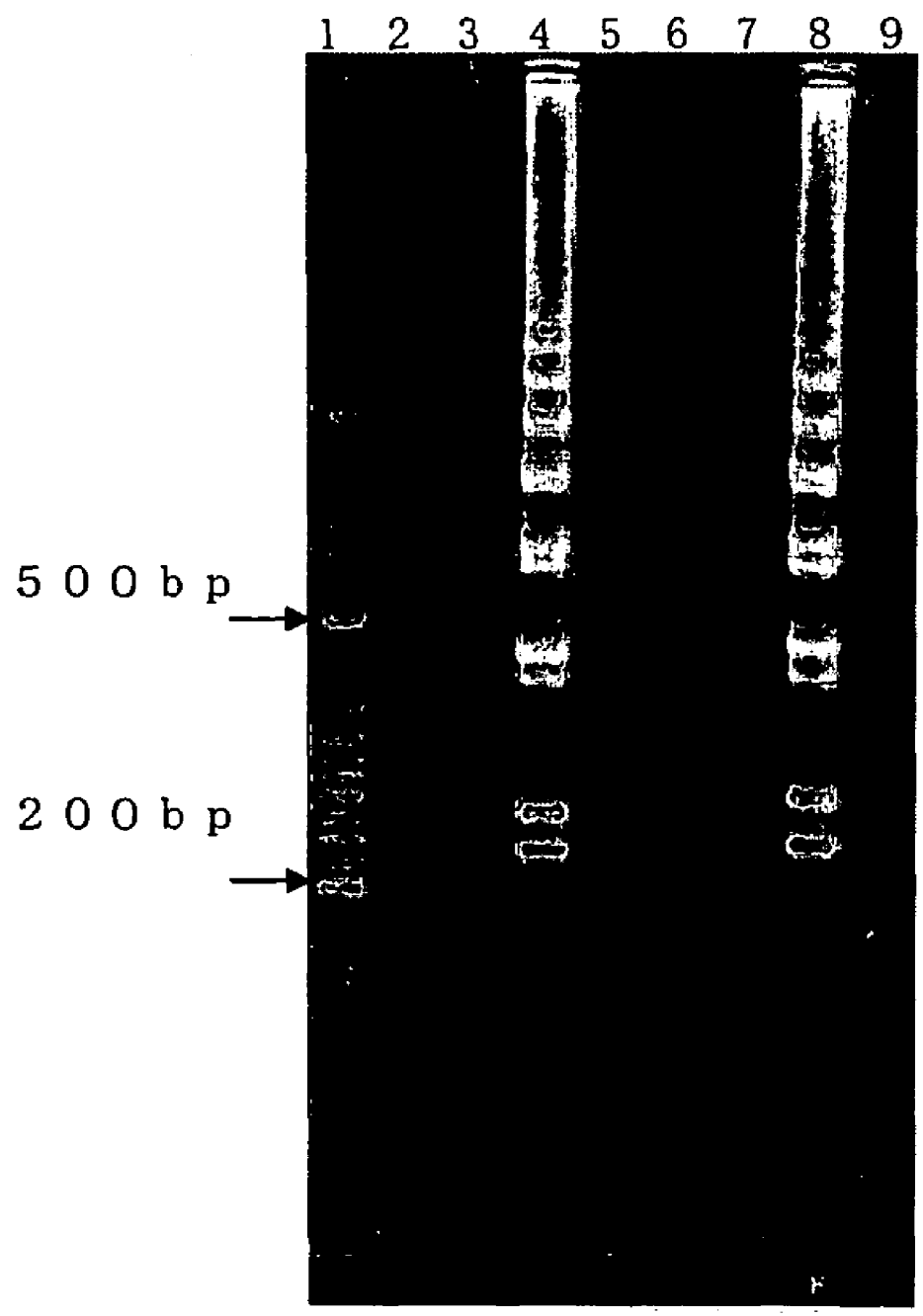
FIG. 10 shows the amplification of an M13mp18RT DNA gene under a variety of conditions.

A 5 µl portion of each mixture was subjected to electrophoresis in 3% NuSieve GTG Agarose (manufactured by BMA; purchased from Takara Bio Inc.; "NuSieve" is the registered trademark of BMA). Results are shown in FIGS. 9 and 10. Samples in respective lanes in these figures are shown in the following Tables 5 and 6.

TABLE 5

Explanation of lanes of electrophoretic photograms in FIG. 9

| Lane | Primer | Template | Reaction Time (min.) |
|---|---|---|---|
| 1 | DNA size marker (20 bp ladder) | | |
| 2 | Primer set 14 | Yes | 60 |
| 3 | Primer set 14 | Yes | 90 |
| 4 | Primer set 14 | Yes | 120 |
| 5 | Primer set 14 | No | 120 |
| 6 | Primer set 15 | Yes | 60 |
| 7 | Primer set 15 | Yes | 90 |
| 8 | Primer set 15 | Yes | 120 |
| 9 | Primer set 15 | No | 120 |
| 10 | Primer set 16 | Yes | 20 |
| 11 | Primer set 16 | Yes | 40 |
| 12 | Primer set 16 | Yes | 60 |
| 13 | Primer set 16 | No | 60 |
| 14 | Primer set 17 | Yes | 20 |
| 15 | Primer set 17 | Yes | 40 |
| 16 | Primer set 17 | Yes | 60 |
| 17 | Primer set 17 | No | 60 |
| 18 | Primer set 18 | Yes | 20 |
| 19 | Primer set 18 | Yes | 40 |
| 20 | Primer set 18 | Yes | 60 |
| 21 | Primer set 18 | No | 60 |

TABLE 6

Explanation of lanes of electrophoretic photograms in FIG. 10

| Lane | Primer | Template | Reaction Time (min.) |
|---|---|---|---|
| 1 | DNA size marker (20 bp ladder) | | |
| 2 | Primer set 19 | Yes | 20 |
| 3 | Primer set 19 | Yes | 40 |
| 4 | Primer set 19 | Yes | 60 |
| 5 | Primer set 19 | No | 60 |
| 6 | Primer set 20 | Yes | 20 |
| 7 | Primer set 20 | Yes | 40 |
| 8 | Primer set 20 | Yes | 60 |
| 9 | Primer set 20 | No | 60 |

In Lanes 5, 9, 13, 17 and 21 of respective Figures, no bands other than those of stained unreacted primers were observed due to the addition of no template.

In Lanes 2 and 3 of FIG. 5, amplified products were obtained in a reaction time of 90 minutes or more. These products, however, was amplified product in the form of ladder which was diferent from the product of aimed size. Primer set 14 is used for the amplification reaction in these lanes. The distance between the region corresponding to the sequence in the 3'-end side of the primer on the extended strand of the primer and the region with which the sequence in the 5'-end side hybridizes is 50 nucleotides in the sense primers and 53 nucleotides in the antisense primers. Thus, when the distance between the region corresponding to the sequence in the 3'-end side of the primer on the extended strand of the primer and the region with which the sequence in the 5'-end side hybridizes becomes excessively large as in Primer set 5, it is considered that the aimed amplification products were not obtained because the folding efficiency of the sequence in the 5'-end side of each primer is lowered significantly and the synthetic reaction according to the invention hardly occurs.

As shown in Lane 7 of FIG. 9, when Primer set 15 was used, it was possible to obtain the aimed amplification product in a reaction time of 90 minutes. Of the low size bands, the band in the vicinity of ca. 240 bp is an expected product of the synthetic reaction of the invention.

Further, as shown in Lanes 12 and 16 of FIG. 9, and Lanes 4 and 8 of FIG. 10, it was possible to obtain the aimed amplification product in a reaction time of 60 minutes when Primer sets 16, 17, 19 and 20 were used. Of the low size bands, the band in the vicinity of ca. 240 bp is an expected product of the synthetic reaction of the invention.

In addition, as shown in Lane 19 of FIG. 9, it was possible to obtain the aimed amplification product in a reaction time of 40 minutes or more when Primer set 18 was used. Of the low size bands, the band in the vicinity of ca. 240 bp is an expected product of the synthetic reaction of the invention.

When the distance between the region corresponding to the sequence in the 3'-end side of the primer on the extended strand of the primer and the region with which the sequence in the 5'-end side hybridizes is small as in Primer set 15, it is considered that a long reaction time is required because most of the sequence on a template having the same sequence to which the next primer is to be annealed remains as a double strand and the subsequent annealing hardly occurs.

Also, when the distance between the region corresponding to the sequence in the 3'-end side of the primer on the extended strand of the primer and the region with which the sequence in the 5'-end side hybridizes is large as in Primer sets 6-11, it is considered that a comparatively long reaction time is required because the folding efficiency of the sequence in the 5'-end side of each primer is lowered.

On the other hand, when the distance between the region corresponding to the sequence in the 3'-end side of the primer on the extended strand of the primer and the region with which the sequence in the 5'-end side hybridizes is not excessively small or excessively large as in Primer set 18, it is considered that the most efficient amplification can be performed in the invention.

Example 4

Of the amplified products obtained in Examples 1-3, the amplified products which were believed to have the highest amplification efficiency were digested with restriction enzymes. A 1 µl portion of the reaction mixture which contained the amplified products obtained with Primer set 5 described in Example 1 was digested with a restriction enzyme MboII, a 1 µl portion of the reaction mixture which contained the amplified products obtained with Primer set 12 described in Example 2 was digested with a restriction enzyme Bst XI, and a 1 µl portion of the reaction mixture which contained the amplified products obtained with Primer set 18 described in Example 3 was digested with a restriction enzyme Pst I. Digestion with restriction enzymes was carried out at a temperature of 37° C. for 3 hours.

Figure 11:
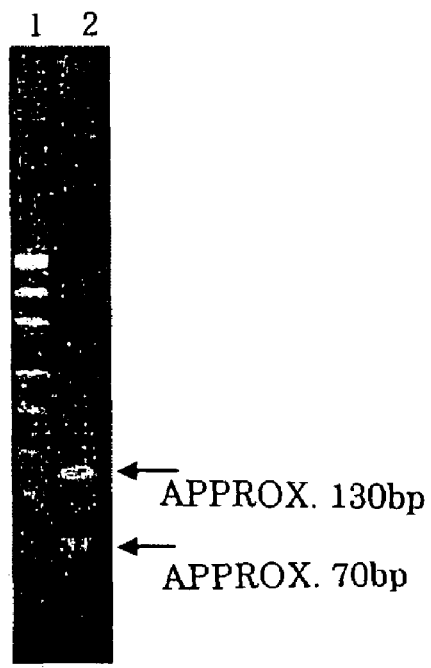
FIG. 11 shows electrophoresis patterns obtained by the treatment of an amplification product from a human STS DYS237 gene with restriction enzymes.

Each of the digestion mixtures was subjected to electrophoresis in 3% NuSieve GTG Agarose (manufactured by BMA; purchased from TAKARA BIO INC.; "NuSieve" is the registered trademark of BMA). Results are shown in FIGS. 11, 12 and 13. Sizes of fragments digested with respective restriction enzymes which are speculated from the respective base sequences are shown in the side of the electrophoretic photograms. It was confirmed from the change of the most part of the undigested bands into the bands having speculated sizes after digestion that the aimed amplified products are obtained.

Example 5

Effects of a Variety of Melting Temperature Adjusting Agents

Amplification reaction was conducted with the addition of a variety of melting temperature adjusting agents into amplification reaction mixtures in order to examine the effects of the melting temperature adjusting agents on amplification efficiency. In the same manner as in Example 1, amplification of a human STS DYS237 gene was attempted by using Human DNA (Clontech) as a template. The primer used was Primer set 5 (SEQ ID NO: 9 and SEQ ID NO: 10) which showed the most preferred amplification efficiency in Example 1.

A reaction mixture (25 µl) of Tris-HCl (20 mM, pH8.8), KCl (10 mM), $(NH_4)_2SO_4$ (10 mM), $MgSO_4$ (8 mM), Triton X-100 (0.1%), dNTP (1.4 mM), the primer pair (1600 nM, resp.), the template DNA, and Bst DNA polymerase (16U; NEW ENGLAND BioLabs) was prepared. The template DNA was added in a concentration of 100 ng, 10 ng, or 0 ng. To this reaction mixture, 6% DMSO, 0.5 M betaine, 4% formamide, or 10% glycerol as the final concentration was added. The mixture was incubated at 60° C. for 90 minutes.

Figure 14:
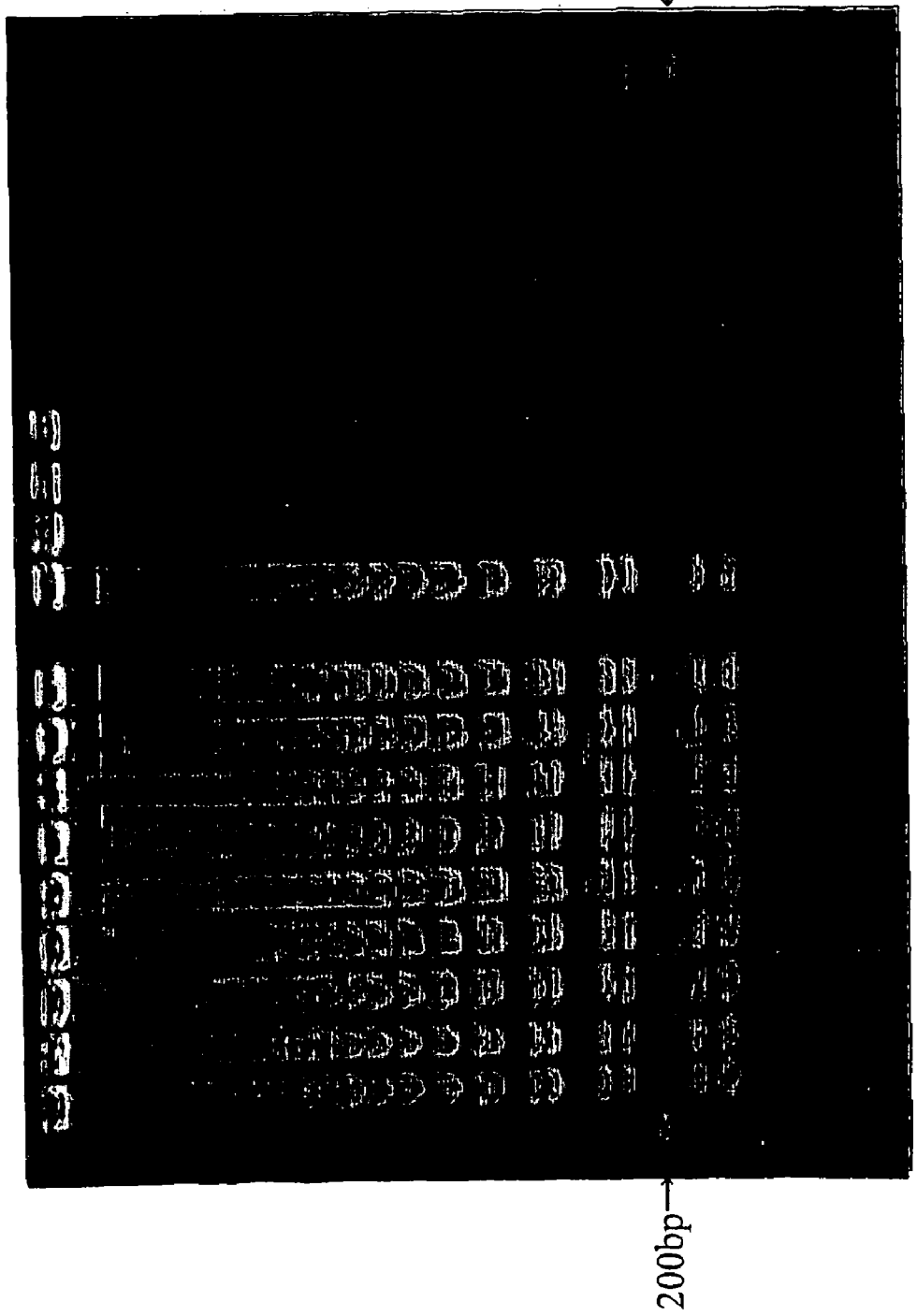
FIG. 14 shows the amplification of a human STS DYS237 gene in the presence of a variety of melting temperature adjusting agents.

After amplification, reaction mixture was subjected to electrophoresis in the same manner as in Example 1. Results are shown in FIG. 14. Samples in respective lanes in FIG. 14 are shown in the following Table 7.

TABLE 7

Explanation of lanes of electrophoretic photograms in FIG. 14

| Lanes | Melting Temperature Adjusting Agents | Amounts of Template |
|---|---|---|
| 1 | DNA size marker (20 bp ladder) | |
| 2 | 6% DMSO | 100 ng |
| 3 | 0.5 M Betaine | 100 ng |
| 4 | 4% Formamide | 100 ng |
| 5 | 10% Glycerol | 100 ng |
| 6 | None | 100 ng |
| 7 | 6% DMSO | 10 ng |
| 8 | 0.5 M Betaine | 10 ng |
| 9 | 4% Formamide | 10 ng |
| 10 | 10% Glycerol | 10 ng |
| 11 | None | 10 ng |
| 12 | 6% DMSO | 1 ng |
| 13 | 0.5 M Betaine | 1 ng |
| 14 | 4% Formamide | 1 ng |
| 15 | 10% Glycerol | 1 ng |
| 16 | None | 1 ng |
| 17 | 6% DMSO | None |
| 18 | 0.5 M Betaine | None |
| 19 | 4% Formamide | None |
| 20 | 10% Glycerol | None |
| 21 | None | None |
| 22 | DNA size marker (20 bp ladder) | |

In FIG. 14, the band in the vicinity of ca. 160 bp is an amplified product expected by the synthetic reaction of the invention. As apparent from FIG. 14, when 100 ng of the template DNA was used, the amplified products were obtained irrespective of the presence or absence of the melting temperature adjusting agents On the other hand, when 10 ng of the template DNA was used, the amplified products were obtained only in the presence of the melting temperature adjusting agents. Moreover, when 1 ng of the template DNA was used, the bands of the amplified products were confirmed only in the presence of the melting temperature adjusting agents, and particularly, the most distinct bands of the amplified products were confirmed in the presence of DMSO (6%) as the melting temperature adjusting agent.

It is believed from the above-described results that amplification efficiency is improved by the addition of the melting temperature adjusting agents such as DMSO, betaine, formamide or glycerol to the reaction mixture, and particularly, the preferred amplification efficiency is obtained by the addition of DMSO.

This application claims priority to JP 2002-314776 filed Oct. 29, 2002, the entirety of which is hereby incorporated by reference.

The invention claimed is:

1. A process for synthesizing a nucleic acid complementary to a target nucleic acid sequence in a template nucleic acid, which comprises the steps of:

(a) annealing a primer to said template nucleic acid and synthesizing a complementary nucleic acid comprising the complementary sequence of said target nucleic acid sequence by a primer extension reaction, wherein the primer comprises in its 3'-end portion a sequence (Ac') that hybridizes to a sequence (A) in the 3'-end portion of the target nucleic acid sequence, and in the 5'-side of said sequence (Ac'), a sequence (B') that hybridizes to the complementary sequence (Bc) of a sequence (B) positioned in the 5'-side of said sequence (A) on the target nucleic acid sequence, wherein in the absence of an intervening sequence between said sequences (Ac') and (B'), X is in the range of 10 to 30, (X−Y)/X is in the range of −1.00 to 0.75, and (X+Y) is in the range of 30 to 50, in which X denotes the number of bases in said sequence (Ac'), and Y denotes the number of bases in a region flanked by said sequences (A) and (B) on the target nucleic acid sequence, and wherein in the presence of an intervening sequence between said sequences (Ac') and (B'), X is in the range of 10 to 30, {X−(Y−Y')}/X is in the range of −1.00 to 0.75, and (X+Y+Y') is in the range of 30 to 50, in which X and Y have the same meanings as above, and Y' denotes the number of bases in said intervening sequence;

(b) hybridizing the sequence (B') positioned in the 5'-side of the complementary nucleic acid synthesized in step (a) with the sequence (Bc) on the same complementary nucleic acid, thereby allowing the portion of said sequence (A) on the template nucleic acid to be single-stranded, and (c) annealing another primer having the same sequence as the primer used in step (a) to the single-stranded sequence (A) portion of the template nucleic acid from step (b) and conducting a strand displacement reaction, thereby displacing the complementary nucleic acid synthesized in step (a) by the complementary nucleic acid newly synthesized with said another primer, and wherein steps (a), (b) and (c) are carried out in an isothermal condition.

2. The process according to claim 1, wherein the double-stranded nucleic acid obtained by step (c) is used repeatedly in step (b).

3. The process according to claim 1, wherein steps (a), (b) and (c) are carried out in an isothermal condition using a primer with a strand length of 15 to 100 nucleotides.

4. The process according to claim 1, wherein a DNA polymerase having strand displacement ability is used.

5. The process according to claim 1, further comprising a step of synthesizing cDNA with a reverse transcriptase when the template nucleic acid is RNA.

6. The process according to claim 1, wherein steps (a), (b) and (c) are carried out in the presence of a melting temperature adjusting agent.

7. The process according to claim 6, wherein the melting temperature adjusting agent is dimethyl sulfoxide, betaine, formamide or glycerol, or a mixture thereof.

8. The process according to claim 1, wherein the target nucleic acid sequence in the template nucleic acid comprises non-natural nucleotide(s).

9. A process for amplifying a target nucleic acid sequence in a double-stranded template nucleic acid, which comprises the steps of:

(a) annealing first and second primers to first and second template nucleic acids of a double-stranded template nucleic acid, respectively, and synthesizing first and second complementary nucleic acids comprising the complementary sequence of said target nucleic acid by a primer extension reaction, respectively, wherein the first primer comprises in its 3'-end portion a sequence (Ac') that hybridizes to a sequence (A) in the 3'-end portion of the target nucleic acid sequence in the first strand of the double-stranded template nucleic acid, and in the 5'-side of said sequence (Ac'), a sequence (B') that hybridizes to the complementary sequence (Bc) of a sequence (B) positioned in the 5'-side of said sequence (A) on said target nucleic acid sequence, wherein in the absence of an intervening sequence between said sequences (Ac') and (B'), X is in the range of 10 to 30, (X−Y)/X is in the range of −1.00 to 0.75, and (X+Y) is in the range of 30 to 50, in which X denotes the number of bases in said sequence (Ac'), and Y denotes the number of bases in a first region flanked by said sequences (A) and (B) on the target nucleic acid sequence, wherein in the presence of an intervening sequence between said sequences (Ac') and (B'), X is in the range of 10 to 30, {X−(Y−Y')}/X is in the range of −1.00 to 0.75, and (X+Y+Y') is in the range of 30 to 50, in which X and Y have the same meanings as above, and Y' denotes the number of bases in said intervening sequence, wherein the second primer comprises in its 3'-end portion a sequence (Cc') that hybridizes to a sequence (C) in the 3'-end portion of the target nucleic acid sequence in the second strand of the double-stranded template nucleic acid, and in the 5'-side of said sequence (Cc') a sequence (D') that hybridizes to the complementary sequence (Dc) of a sequence (D) positioned in the 5'-side of said sequence (C) on said target nucleic acid sequence, wherein in the absence of an intervening sequence between said sequences (Cc') and (D'), X is in the range of 10 to 30, (X−Y)/X is in the range of −1.00 to 0.75, and (X+Y) is in the range of 30 to 50, in which X denotes the number of bases in said sequence (Cc'), and Y denotes the number of bases in a second region flanked by said sequences (C) and (D) on the target nucleic acid sequence, and wherein in the presence of an intervening sequence between said sequences (Cc') and (D'), X is in the range of 10 to 30, {X−(Y−Y')}/X is in the range of −1.00 to 0.75, and (X+Y+Y') is in the range of 30 to 50, in which X and Y have the same meanings as above, and Y' denotes the number of bases in said intervening sequence;

(b) hybridizing the sequences (B') and (D') positioned in the 5'-side of the first and second complementary nucleic acids synthesized in step (a) with the sequences (Bc) and (Dc) on the same complementary nucleic acid, respectively, thereby converting the portions of said sequences (A) and (C) on the first and second template strands, respectively, to single-stranded form, and (c) annealing additional primers having the same sequence as said primers used in step (a) to the single-stranded sequence (A) and (C) portions of the first and second template nucleic acids from step (b) and conducting a strand displacement reaction, thereby displacing the first and second complementary nucleic acid synthesized in step (a) by the complementary nucleic acids newly synthesized with said additional primers, and wherein steps (a), (b) and (c) are carried out in an isothermal condition.

10. The process according to claim 9, wherein the double-stranded nucleic acids obtained by step (c) are used repeatedly in step (b).

11. The process according to claim 9, wherein the first and second complementary nucleic acids obtained as single strands by step (c) are used repeatedly as the second and first template nucleic acids, respectively, in step (a).

12. The process according to claim 9, wherein a DNA polymerase having strand displacement ability is used.

13. The process according to claim 9, further comprising a step of synthesizing cDNA with a reverse transcriptase when the template nucleic acid is RNA.

14. The process according to claim 9, wherein steps (a), (b) and (c) are carried out in the presence of a melting temperature adjusting agent.

15. The process according to claim 14, wherein the melting temperature adjusting agent is dimethyl sulfoxide, betaine, formamide or glycerol, or a mixture thereof.

16. The process according to claim 9, wherein the target nucleic acid sequence in the double-stranded template nucleic acid comprises non-natural nucleotide(s).

* * * * *

UNITED STATES PATENT AND TRADEMARK OFFICE
CERTIFICATE OF CORRECTION

PATENT NO. : 7,803,579 B2
APPLICATION NO. : 10/532975
DATED : September 28, 2010
INVENTOR(S) : Mitani et al.

It is certified that error appears in the above-identified patent and that said Letters Patent is hereby corrected as shown below:

Front page of patent, (56) References Cited; U.S. PATENT DOCUMENTS; the following should be added:

| | | |
|---|---|---|
| 4,672,040 | 6/1987 | Josephson |
| 4,683,195 | 7/1987 | Mullis et al. |
| 4,683,202 | 7/1987 | Mullis |
| 4,800,159 | 1/1989 | Mullis et al. |
| 4,849,336 | 7/1989 | Miyoshi et al. |
| 5,512,439 A | 4/1996 | Hornes et al. |
| 5,824,517 A | 10/1998 | Cleuziat et al. |
| 6,046,807 A | 4/2000 | Chandler |
| 6,057,107 A | 5/2000 | Fulton |
| 6,063,603 A | 5/2000 | Davey et al. |
| 6,117,635 A | 9/2000 | Nazarenko et al. |
| 6,366,354 B1 | 4/2002 | Chandler |
| 6,420,539 B1 | 6/2002 | Kramer et al. |
| 6,617,106 B1 | 9/2003 | Benner |
| 2003/0073081 A1 | 4/2003 | Mukai et al. |
| 2003/0207292 A1 | 11/2003 | Notomi et al. |

Front page of patent, (56) References Cited; FOREIGN PATENT DOCUMENTS; the following should be added:

| | | | |
|---|---|---|---|
| EP | 0 320 308 | A2 | 6/1989 |
| EP | 0 971 039 | A2 | 1/2000 |
| EP | 1 041 160 | A1 | 10/2000 |
| EP | 1 072 678 | A1 | 1/2001 |
| EP | 1 327 679 | A1 | 9/2001 |
| EP | 1 158 047 | A1 | 11/2001 |
| JP | 59- 93099 | A | 5/1984 |
| JP | 59-148798 | A | 8/1984 |

(Continued)

Signed and Sealed this
Thirty-first Day of May, 2011

David J. Kappos
*Director of the United States Patent and Trademark Office*

| | | | |
|---|---|---|---|
| JP | 59-204200 | A | 11/1984 |
| JP | 4-501959 | A | 4/1992 |
| JP | 7- 6986 | A | 1/1995 |
| JP | 7-114718 | B2 | 12/1995 |
| JP | 9-504699 | A | 5/1997 |
| JP | 2650159 | B2 | 5/1997 |
| JP | 10-257900 | A | 9/1998 |
| JP | 2710159 | B2 | 10/1998 |
| JP | 2000-245460 | A | 9/2000 |
| JP | 2000-300265 | A | 10/2000 |
| WO | 95/12689 | A1 | 5/1995 |
| WO | 95/25180 | A1 | 9/1995 |
| WO | 99/06591 | A1 | 2/1999 |
| WO | 99/09211 | A1 | 2/1999 |
| WO | 99/10369 | A1 | 3/1999 |
| WO | 99/54455 | A1 | 10/1999 |
| WO | 00/28082 | A1 | 5/2000 |
| WO | 00/63691 | A2 | 10/2000 |
| WO | 01/34838 | A1 | 5/2001 |

Front page of patent, (56) References Cited; OTHER PUBLICATIONS; the following should be added:

AU, et al. "Initiation of Methyl-directed Mismatch Repair." The Journal of Biological Chemistry, vol. 267(17) June 1992, pp 12142-12148

CLARK et al. "Functional Interaction of Proliferating Cell Nuclear Antigen with HSH2-MSH6 and MSH2-MSH3 Complexes." The Journal of Biological Chemistry, vol. 275(47), November 2000, pp. 36498-36501

DENG et al. "Site-Directed Mutagenesis of Virtually any plasmid by Eliminating a Unique Site." Analytical Biochemistry 200, 1992, pp. 81-88

DIAZ et al. "PCR-Mediated Chemical Mutagenesis of Cloned Duplex DNAs." BioTechniques, vol. 11(2), 1991, DOHET et al. "Large non-homology in heteroduplex DNA is processed differently than single base pair mismatches." Mol Gen Gent, 206, 1987, pp. 181-184

GOTOH et al. "Rapid method for detection of point mutations using mismatch binding protein (MutS) and an optical biosensor." Genetic Analysis: Biomolecular Engineering, 14, 1998, pp. 47-50

HABER et al. "Nucleotide Sequence of the Salmonella typhimurium mutS Gene Required for Mismatch Repair: Homology of MutS and HexA of Streptococcus pneumoniae." Journal of Bacteriology, vol. 170(1), January 1988, pp. 197-202

HORLACHER et al. "Recognition by viral and cellular DNA polymerases of nucleosides bearing bases with nonstandard hydrogen bonding patterns." Proc. Natl. Acad. Sci. USA, vol. 92, July 1995, pp. 6329-6333

(Continued)

JIRICNY et al., "Mismatch-containing oligonucleotide duplexes bound by the E.coli mutS-encoded protein." Nucleic Acids Research, vol. 16(16), 1988, pp. 7843-7853

JONES et al. "Repair of a Mismatch is Influenced by the Base composition of the Surrounding Nucleotide Sequence", Genetics, 115, April 1987, pp. 605-610

LAHUE et al. "DNA Mismatch Correction in a Defined System", Science, vol. 245, July 1989, pp. 160-164

LAHUE et al. "Methyl-directed DNA mismatch repair in Escherichia coli." Mutation Research, 198, 1988 pp 37-43

LARRICK "Message Amplification Phenotyping (MAPPing) – principles, practice and potential." TIBTECH, vol. 10, May 1992, pp. 146-152

LU et al. "Repair of Single Base-Pair Transversion Mismatches of Escherichia coli in Vitro: Correction of Certain A/G Mismatches Is Independent of dam Methylation and Hose mutHLS Gene Functions." Genetics, 118, April 1988, pp. 593-600

LUTZ et al. "Recognition of a Non-Standard Base Pair by Thermostable DNA Polymerases." Bioorganic & Medicinal Chemistry Letters 8, 1998, pp. 1149-1152

MODRICH "Methyl-directed DNA Mismatch Correction." The Journal of Biological Chemistry, vol. 264(12), 1989 pp. 6597-6600

NAKAMAYE et al. "Inhibition of restriction endonuclease Nci I cleavage by phosphorothioate groups and is application to oligonucleotide-directed mutagensis." Nucleic Acids Research, vol. 14(24), 1986, pp. 9679-9698

PANG et al. "Identification and Characterization of the mutL and mutS Gene Products of Salmonella typhimurium LT2." Journal of Bacteriology, vol. 163(3), September 1985, pp. 1007-1015

PRIEBE et al. "Nucleotide Sequence of the hexA Gene for DNA Mismatch Repair in Streptococcus pnuemoniae and Homology of hexA to mutS of Escherichia coli and salmonella typhimurium." Journal of Bacteriology, vol. 170(1), January 1988, pp. 190-196

RADMAN et al. "The High Fidelity of DNA Duplication." Scientific American, August 1988, pp. 24-30

RADMAN et al. "Mismatch Repair in ESCHERICHIA COLI." Ann. Rev. Genet., 20, 1896, pp. 523-538

SAMBROOK et al. "Conditions for Hybridization of Oligonucleotide Probes", Molecular Cloning: A Laboratory Manual, 2nd edition, Cold Spring Harbor Laboratory Press, 1989, pp. 11.45-11.57

SISMOUR et al. "First PCR amplification of DNA containing a non-standard base pair", Biochemistry, vol. 42 (28), 2003, p. 8598

SMITH et al. "Mutation detection with MutH, MutL, and MutS mismatch repair proteins." Proc. Natl. Acad. Sci. USA, vol. 93, April 1996, pp. 4374-4379

SU et al. "Mispair Specificity of Methyl-directed DNA Mismatch Correction in Vitro", The Journal of Biological Chemistry, vol. 263(14), May 1988, pp. 6829-6835

FABRICE et al. "Une méthode d'amplification génique isotherme." C.R. Acad. Sci. Paris, Sciences de la vie 321, 1998, pp. 909-914.

SAMBROOK et al. "Conditions for Hybridization of Oligonucleotide Probes", Molecular Cloning: A Laboratory Manual, 2nd edition, Cold Spring Harbor Laboratory Press, 1989, pp. 8.2-8.17

(Continued)

CERTIFICATE OF CORRECTION (continued)
U.S. Pat. No. 7,803,579 B2

LOWE et al. "A Computer Program for Selection of oligonucleotide primers for polymerase chain reactions." Nucleic Acids Research, col. 18(7), 1990, pp. 1757-1761.
ROBERTSON et al. "An Introduction to PCR Primer Design and Optimization of Amplification Reactions." Forensic DNA Profiling Protocols; Methods in Molecular Biology, vol. 98, 1998, pp. 121-154.
HYNDMAN et al. "PCR Primer Design." PCR Protocols Part III, Methods in Molecular Biology, vol. 226, 2003, pp. 81-88.
VAN PELT-VERKUIL et al. Principles and Technical Aspects of PCR Amplification; Chapter 5: PCR Primers." 2008, pp. 63-90.
PUSKÁS et al. "Reduction of mispriming in amplification reactions with restricted PCR." Genome Research, 5(3), 1995, pp. 309-311.
HAFF "Improved quantitative PCR using nested primers." PCR Methods Appl., 3, 1994, pp. 332-337.
GOOKIN et al. "Single-Tube Nested PCR for Detection of Tritrichomonas foetus in Feline Feces. Journal of Clinical Microbiology, vol. 40(11), 2002, pp. 4126-4130.
CHAN et al. "Single-tube nested CPR in the diagnosis of tuberculosis." Journal of Clinical Pathology, vol. 49(4), 1996, 290-294.
WOLFF et al. "Single-tube nested PCR with room-temperature-stable reagents." RCR Methods Appl, 4(6), 1995, pp. 376-379.
ENOSAWA et al. "Use of Loop-Mediated Isothermal Amplifications of the IS900 Sequence for Rapid Detection of Cultured Mycobacterium avium subsp. paratuberculosis." Journal of Clinical Microbiology, 41(9), September 2003, pp. 4359-4365.

Front page of patent, (56) References Cited; FOREIGN PATENT DOCUMENTS;
JP 3-313358 B2: "12/2002" should read -- 8/2002 --.

Front page of patent, (56) References Cited; OTHER PUBLICATIONS;
5th citation (Nagamine): "Accelerateed" should read -- Accelerated --.

Column 6, line 65, "Bacid" should read -- acid --.
Column 8, line 11, "acid The" should read -- acid. The --.
Column 9, line 46, "oligonucleotideprimers" should read -- oligonucleotide primers --.
Column 9, line 66, "→" should read -- > --.
Column 10, line 13, "9° Nm" should read -- 9°Nm --.
Column 11, line 9, "Bca(exo-)" should read -- Bca (exo-) --.
Column 12, line 54, "9° N" should read -- 9°N --.
Column 16, line 8, "can-be" should read -- can be --.
Column 21, line 10, "5-was" should read -- 5 was --.
Column 21, line 49, "sequenceplaced" should read -- sequence placed --.
Column 26, line 7, "diferent" should read -- different --.